(12) United States Patent
Robert et al.

(10) Patent No.: US 10,258,711 B2
(45) Date of Patent: *Apr. 16, 2019

(54) DIFFUSION DEVICE WITH REPLACEABLE CARTRIDGE

(71) Applicant: Prolitec, Inc., Milwaukee, WI (US)

(72) Inventors: Marc Robert, Mukwonago, WI (US); Richard Weening, West Palm Beach, FL (US)

(73) Assignee: Prolitec, Inc., Milwaukee, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/605,898

(22) Filed: Jan. 26, 2015

(65) Prior Publication Data

US 2016/0303269 A1    Oct. 20, 2016
US 2018/0161472 A9    Jun. 14, 2018

Related U.S. Application Data

(63) Continuation of application No. 11/734,660, filed on Apr. 12, 2007, now Pat. No. 8,939,386.

(51) Int. Cl.
| | |
|---|---|
| *F16N 7/34* | (2006.01) |
| *A61M 11/06* | (2006.01) |
| *A61M 16/16* | (2006.01) |
| *A61L 9/14* | (2006.01) |
| *B05B 7/30* | (2006.01) |

(52) U.S. Cl.
CPC ............... *A61L 9/14* (2013.01); *B05B 7/30* (2013.01); *A61L 2209/133* (2013.01); *A61M 11/06* (2013.01); *A61M 16/16* (2013.01); *F16N 7/34* (2013.01)

(58) Field of Classification Search
CPC ....... A61L 9/14; A61L 2209/133; B05B 7/30; A61M 11/06; A61M 16/16; F16N 7/34
USPC ....... 239/338, 346, 340, 106, 290, 318, 349, 239/352, 369, 375, 412, 413, 427.3, 430
See application file for complete search history.

(56) References Cited

U.S. PATENT DOCUMENTS

| | | | |
|---|---|---|---|
| 1,592,982 | A | 7/1924 | Loepsinger |
| 2,057,434 | A | 10/1936 | Jaden et al. |
| 2,565,691 | A | 8/1951 | Ketelsen |
| 2,635,921 | A | 4/1953 | Deutsch |
| 2,718,934 | A | 9/1955 | Norgren |
| 2,747,688 | A | 5/1956 | Faust |
| 2,751,045 | A | 6/1956 | Faust |
| 2,778,619 | A | 1/1957 | Goodyer |
| 2,890,765 | A | 6/1959 | Friedel |
| 3,101,160 | A | 8/1963 | Picot |
| 3,302,374 | A | 2/1967 | Szekely |

(Continued)

FOREIGN PATENT DOCUMENTS

| | | |
|---|---|---|
| JP | 2005066593 | 3/2005 |
| WO | WO2004080604 | 9/2004 |

*Primary Examiner* — Jason J Boeckmann
*Assistant Examiner* — Steven M Cernoch
(74) *Attorney, Agent, or Firm* — Nicholas A. Kees; Godfrey & Kahn, S.C.

(57) ABSTRACT

A removable replaceable cartridge for use with a liquid diffusing device. The cartridge includes a venturi, a conduit extending to the venturi, a mixing area and an outlet path for atomizing and dispersing a liquid within the cartridge. A diffusion device including a removable replaceable cartridge received within a housing. The housing includes a source of compressed gas which is directed into the cartridge. A venturi head with a unitary body for use with a diffusion device.

2 Claims, 49 Drawing Sheets

(56) References Cited

U.S. PATENT DOCUMENTS

| | | | |
|---|---|---|---|
| 3,349,042 A | | 10/1967 | Andrews |
| 3,506,589 A | | 4/1970 | Hoffman |
| 4,087,048 A | | 5/1978 | Smrt |
| 4,131,658 A | | 12/1978 | Hirata et al. |
| 4,174,811 A | | 11/1979 | Binder et al. |
| 4,222,525 A | | 9/1980 | Hildebrandt |
| 4,243,396 A | * | 1/1981 | Cronenberg ............ A61M 11/06 128/203.16 |
| 4,629,590 A | * | 12/1986 | Bagwell ................ A61M 16/16 128/200.21 |
| 4,767,576 A | | 8/1988 | Bagwell |
| 4,781,329 A | | 11/1988 | Tenney et al. |
| 4,990,290 A | | 2/1991 | Gill et al. |
| 5,165,604 A | * | 11/1992 | Copp, Jr. .............. B05B 7/0087 239/106 |
| 5,873,530 A | | 2/1999 | Chizinsky |
| 6,021,776 A | | 2/2000 | Allred et al. |
| 6,405,944 B1 | | 6/2002 | Benalikhoudja |
| 6,837,447 B1 | | 1/2005 | Clark |
| 7,448,557 B2 | | 11/2008 | Ray et al. |
| 7,712,683 B2 | * | 5/2010 | Robert ...................... A61L 9/14 239/338 |
| 8,939,386 B2 | * | 1/2015 | Robert ...................... A61L 9/14 239/338 |
| 2004/0050963 A1 | | 3/2004 | Ray |
| 2004/0256484 A1 | | 12/2004 | Joseph |
| 2004/0256485 A1 | | 12/2004 | Joseph |
| 2005/0025895 A1 | | 2/2005 | Takeuchi |
| 2006/0151630 A1 | | 7/2006 | Joseph |
| 2006/0157589 A1 | | 7/2006 | Joseph |
| 2006/0219814 A1 | | 10/2006 | Benalikhoudja |
| 2006/0237090 A1 | | 10/2006 | Benalikhoudja |

* cited by examiner

DIFFUSION DEVICE WITH REPLACEABLE CARTRIDGE

CROSS-REFERENCE TO RELATED APPLICATIONS

This application is a continuation of U.S. patent application Ser. No. 11/734,660, filed on Apr. 12, 2007, the disclosure of which is incorporated herein by reference.

BACKGROUND

Diffusion devices in the past have had the ability to dispense scent or other liquids throughout the atmosphere of desired spaces but have suffered from several drawbacks. Changing the scent or product that is being diffused has typically required that a reservoir of the diffusing device be emptied and then filled with the new liquid or scent. Conventional reservoirs may be configured to be refilled directly with the liquid to be diffused, which can be messy or have a highly concentrated odor. This refilling may not be desirably carried out in a public setting, such as a store, restaurant, casino or other commercial setting where the scent or other product may be diffused.

Additionally, having to deal with bulk refills that must be poured or otherwise placed into the reservoir of the diffusion device may not be a desirable arrangement for home or non-commercial diffusion devices. An improved ability to refill or recharge a diffusion device with scent or other product is desirable.

Conventional diffusion devices may require that a liquid reservoir be emptied before a new scent or other product may be added to the device for diffusion. Unless the reservoir and perhaps other portions of the apparatus that perform the diffusion are cleaned of any residual of the prior diffused material, at least some degree of cross-contamination between the different scents or other products to be diffused is likely to occur when changing scents. Improvements permitting quick and easy shifting between scents and/or other products to be diffused is desirable.

Conventional diffusion devices may include a diffusion head with a venturi within which mixing of the liquid to be dispersed and pressurized gases take place prior to the liquid being released into the area to be treated. Openings and passages within these diffusion heads may be quite small and susceptible to clogging or blockage by contaminants or larger particles within the liquid to be diffused. Periodic cleaning or replacement of the diffusion heads may sometimes be necessary to ensure efficient operation of the diffusion device. Improvement in the ease with which diffusion heads may be replaced is desirable.

SUMMARY

The present disclosure relates generally to liquid diffusion devices. More specifically, the present disclosure relates to a removable replaceable cartridge for use with a diffusion device where the liquid to be diffused is contained within the cartridge. The present disclosure further relates to a diffusion device including a removable replaceable cartridge received within a housing. The housing includes a source of compressed gas which is directed into the cartridge. The removable replaceable cartridge includes a tube, venturi, mixing areas and outlet paths for diffusing and dispersing a liquid within the cartridge. The present disclosure further relates to a unitary diffusion head for use with a diffusion device, the head including a gas conduit and a liquid conduit in fluid communication with a venturi.

BRIEF DESCRIPTION OF THE DRAWINGS

The accompanying drawing figures, which are incorporated in and constitute a part of the description, illustrate several aspects of the invention and together with the description, serve to explain the principles of the invention. A brief description of the figures is as follows:

FIG. 1 is a perspective view of a liquid diffusion device according to the present disclosure.

FIG. 2 is a top view of the liquid diffusion device of FIG. 1.

FIG. 3 is a perspective view of the liquid diffusion device of FIG. 1 with a cover exploded.

FIG. 4 is a perspective view of the liquid diffusion device of FIG. 1 with the cover removed.

FIG. 5 is a perspective view of a liquid cartridge for use with the liquid diffusion device of FIG. 1.

FIG. 6 is a top view of the cartridge of FIG. 5.

FIG. 7 is a bottom view of the cartridge of FIG. 5.

FIG. 8 is a first exploded perspective view of the cartridge of FIG. 5, with a tube and venturi assembly removed for clarity.

FIG. 9 is a second exploded perspective view of the cartridge of FIG. 8.

FIG. 10 is an exploded side view of the cartridge of FIG. 8.

FIG. 11 is a top perspective view of a top cap for the cartridge of FIG. 8.

FIG. 12 is a bottom perspective view of the top cap of FIG. 11.

FIG. 13 is a top view of the top cap of FIG. 11.

FIG. 14 is a bottom view of the top cap of FIG. 11.

FIG. 15 is a perspective view of a baffle of the cartridge of FIG. 8.

FIG. 16 is a top view of the baffle of FIG. 15.

FIG. 17 is a bottom view of the baffle of FIG. 15.

FIG. 18 is a first side view of the baffle of FIG. 15.

FIG. 19 is a second side view of the baffle of FIG. 15.

FIG. 20 is a side cross-section view of the baffle of FIG. 15, taken along line 20-20 of FIG. 16.

FIG. 21 is a perspective view of a reservoir of the cartridge of FIG. 8.

FIG. 22 is a top perspective view of the reservoir of FIG. 21.

FIG. 23 is a perspective view of a prior art one way flow device of the cartridge of FIG. 8.

FIG. 24 is a front perspective view of the prior art one way flow device of FIG. 23.

FIG. 25 is a side perspective view of a tube and venturi assembly of the cartridge of FIG. 8.

FIG. 26 is a side view of the tube and venturi assembly of FIG. 25.

FIG. 27 is an exploded side view of the tube and venturi assembly of the cartridge of FIG. 25.

FIG. 28 is a side cross-sectional view of the tube and venturi assembly of the cartridge of FIG. 25.

FIG. 29 is a front cross-sectional view of the tube and venturi assembly of FIG. 25.

FIG. 30 is a bottom view of the tube and venturi assembly of FIG. 25.

FIG. 31 is a perspective view of the nozzle cap of venturi assembly of FIG. 25.

FIG. 32 is a first side view of the nozzle cap of FIG. 31.

FIG. 33 is a second side view of the nozzle cap of FIG. 31.

DETAILED DESCRIPTION

Reference will now be made in detail to exemplary aspects of the present invention which are illustrated in the accompanying drawings. Wherever possible, the same reference numbers will be used throughout the drawings to refer to the same or like parts.

Figure 1:
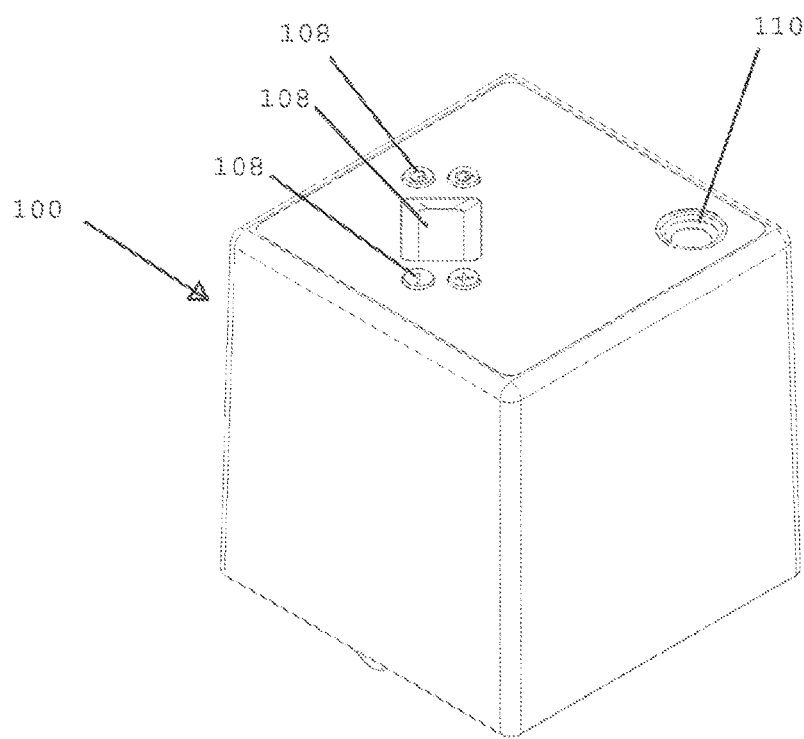
Figure 2:
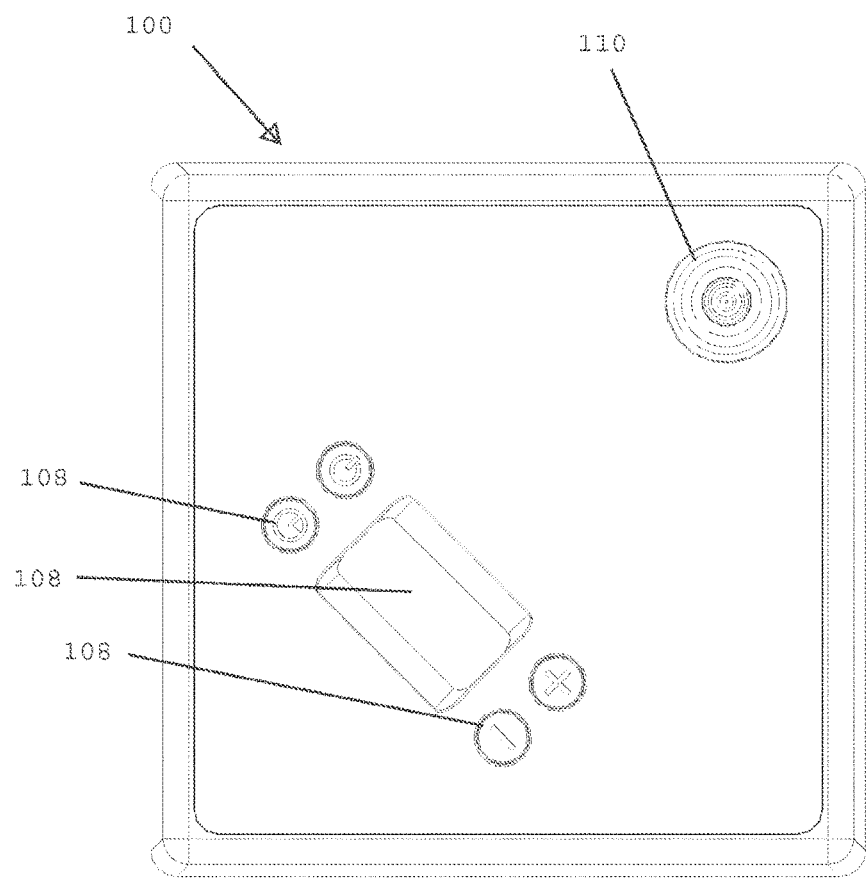
Figure 3:
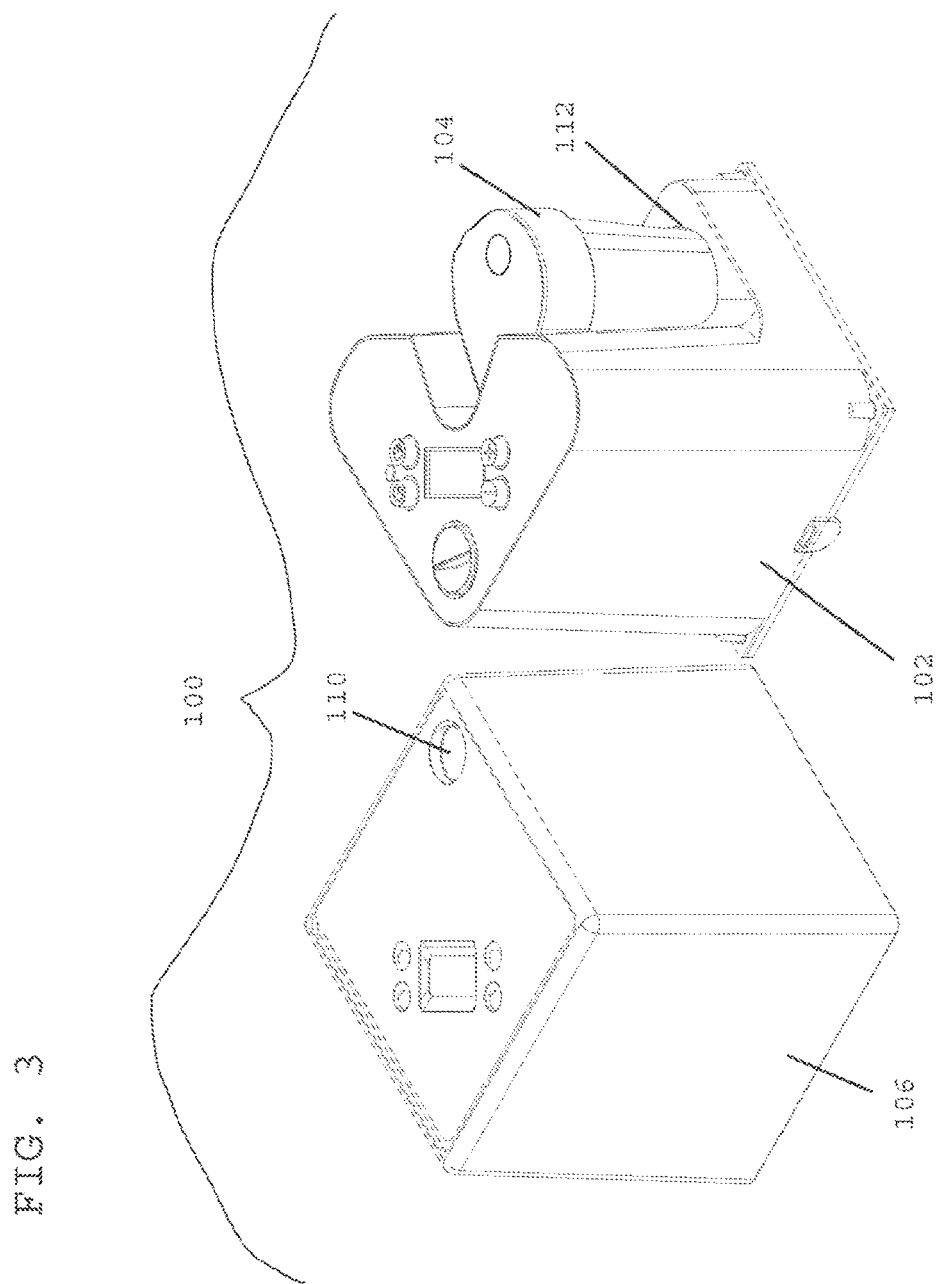
Figure 4:
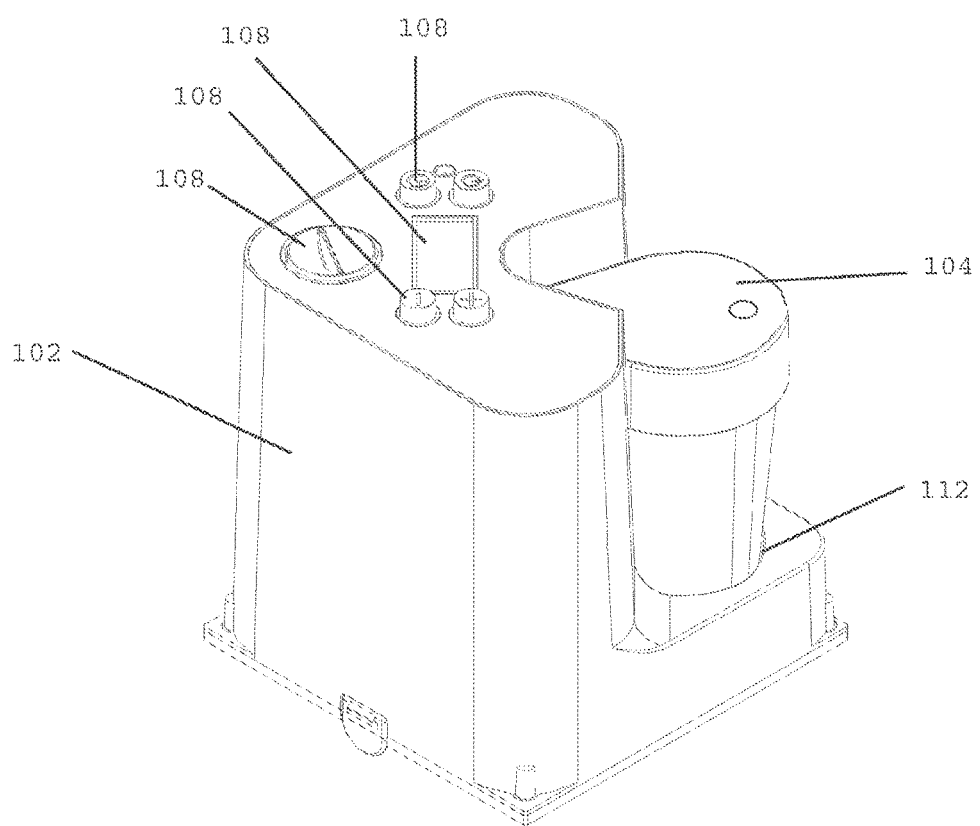
Figure 5:
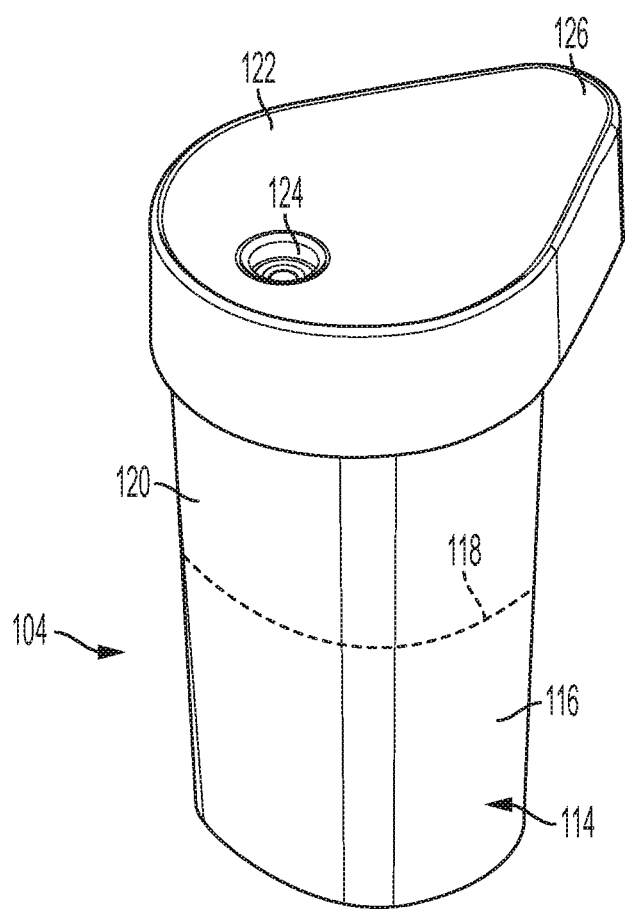
Figure 6:
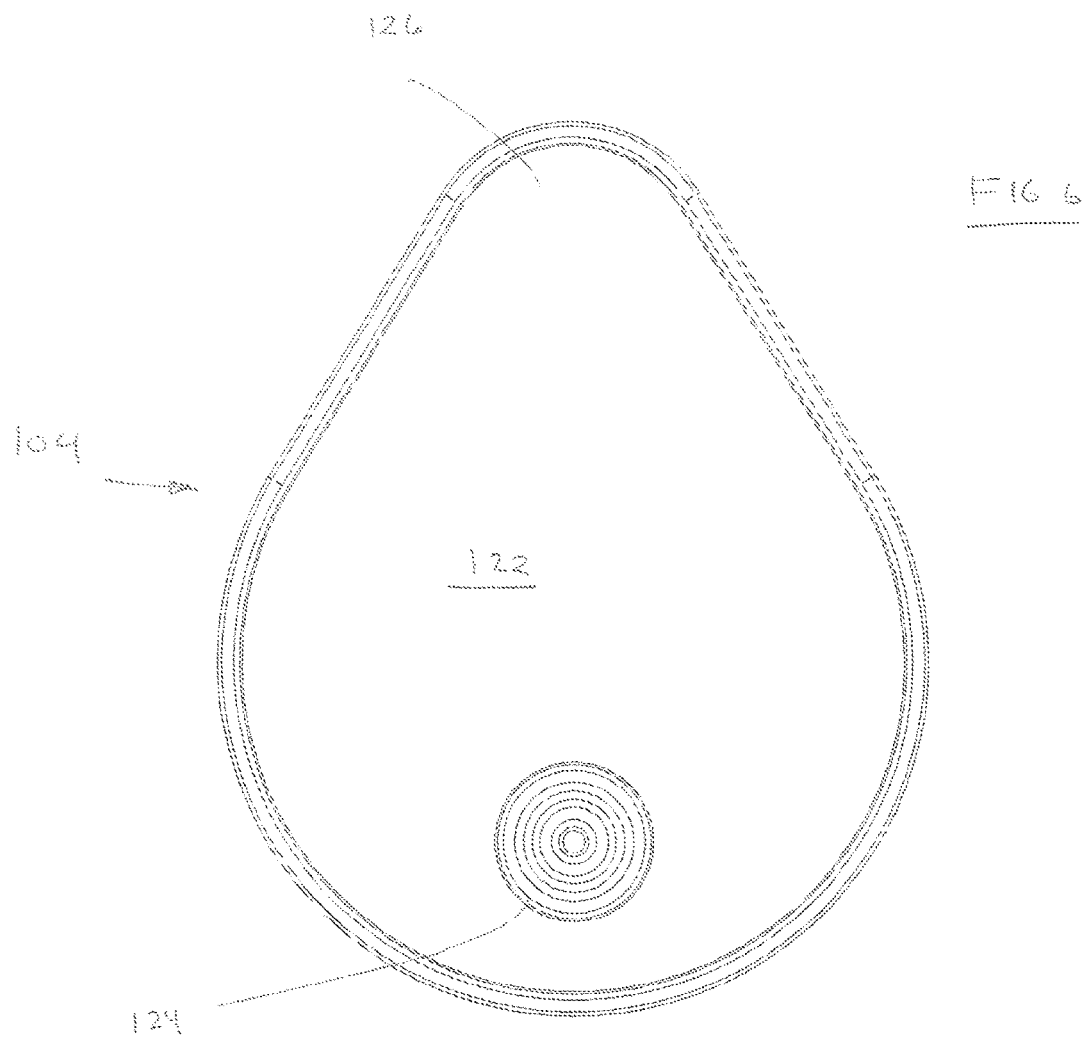
Figure 7:
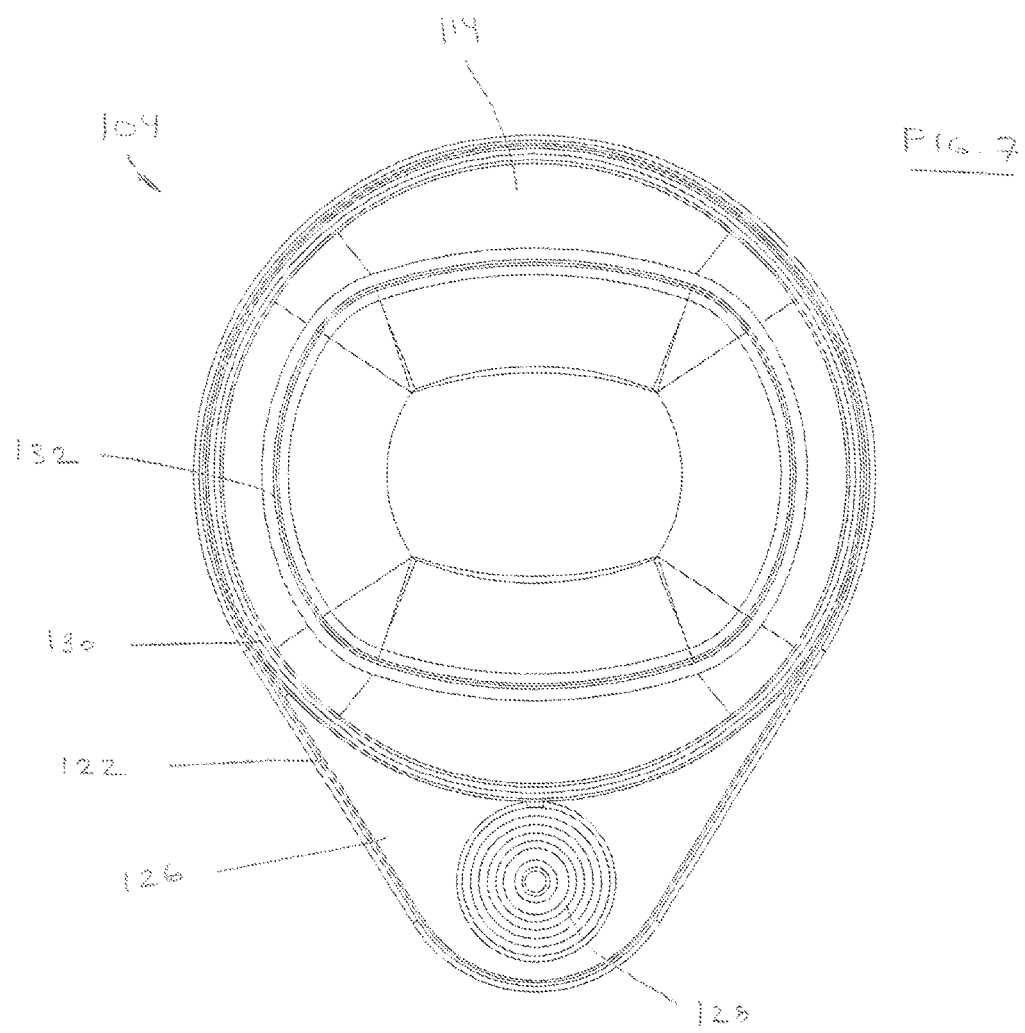
Figure 8:
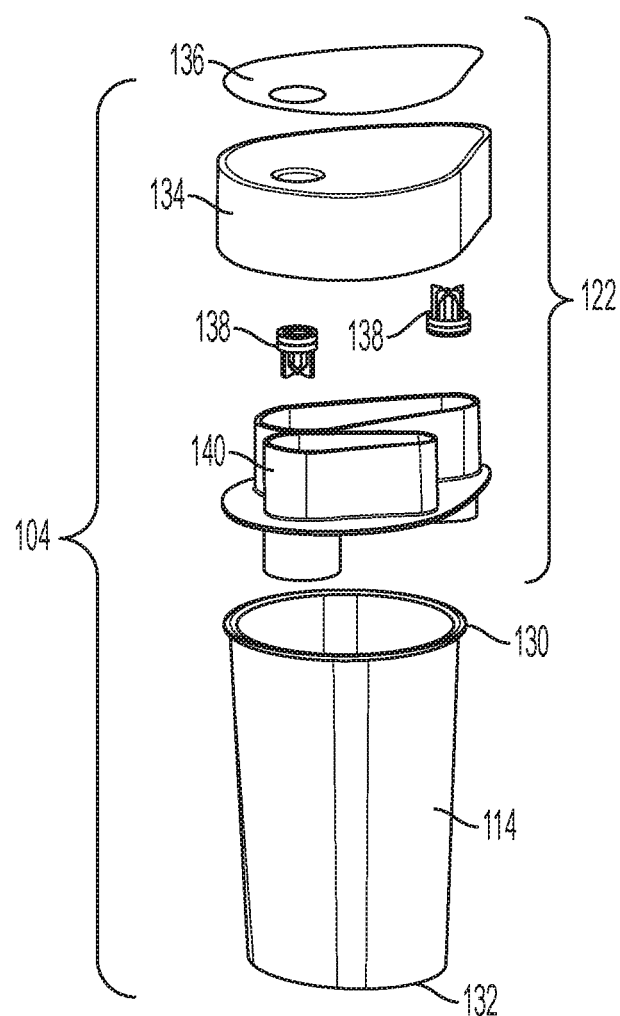
Figure 9:
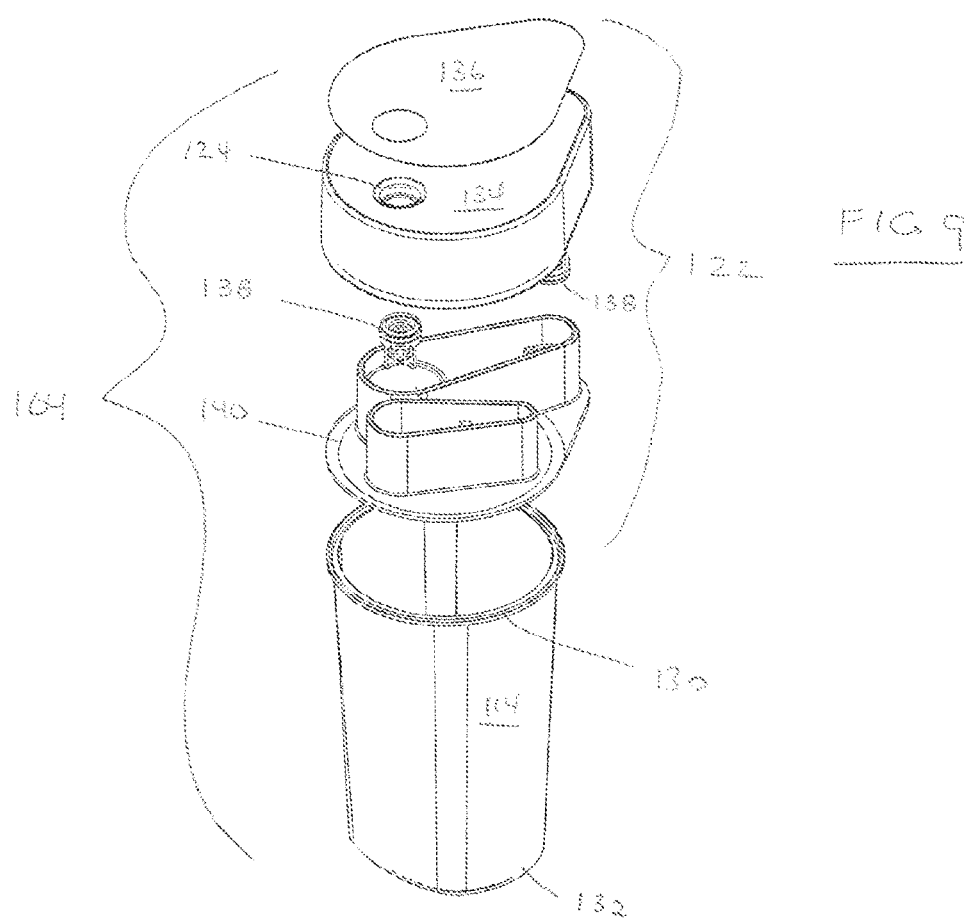
Figure 10:
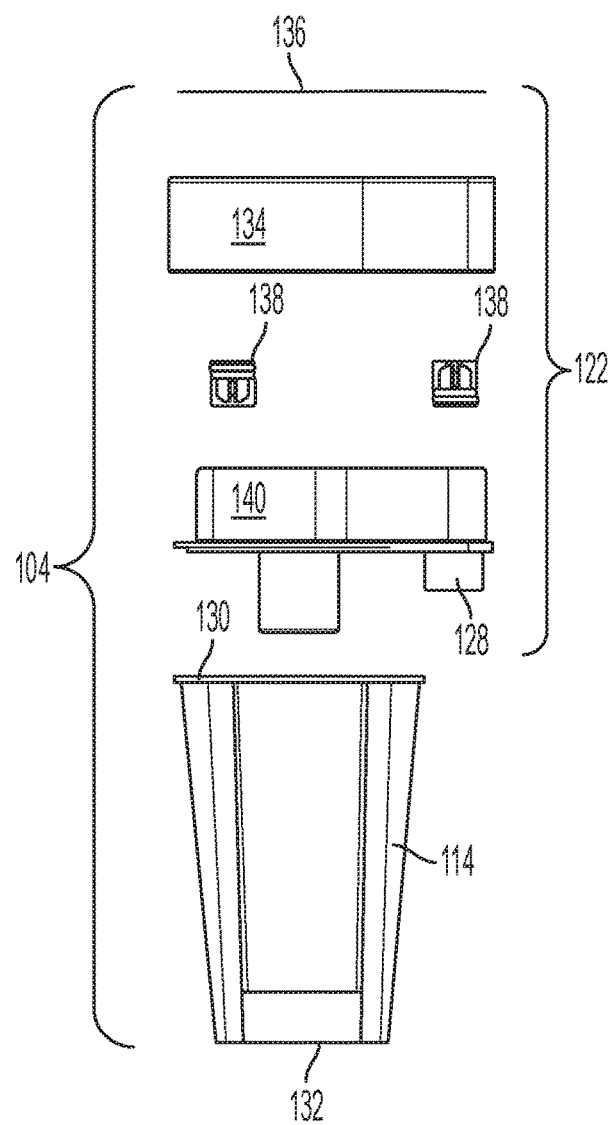
Figure 11:
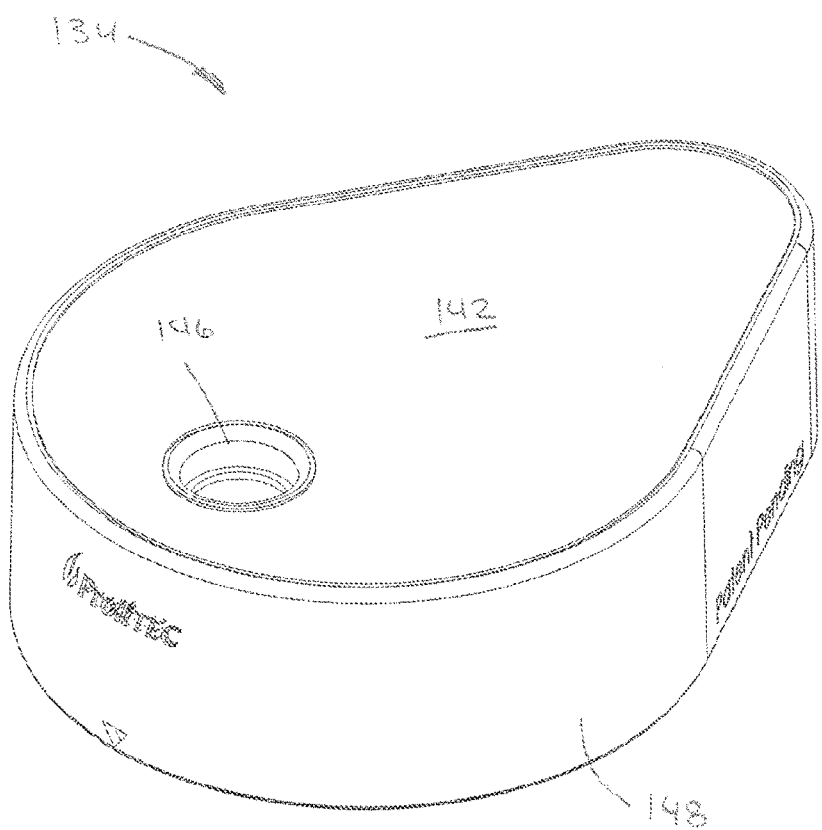
Figure 12:
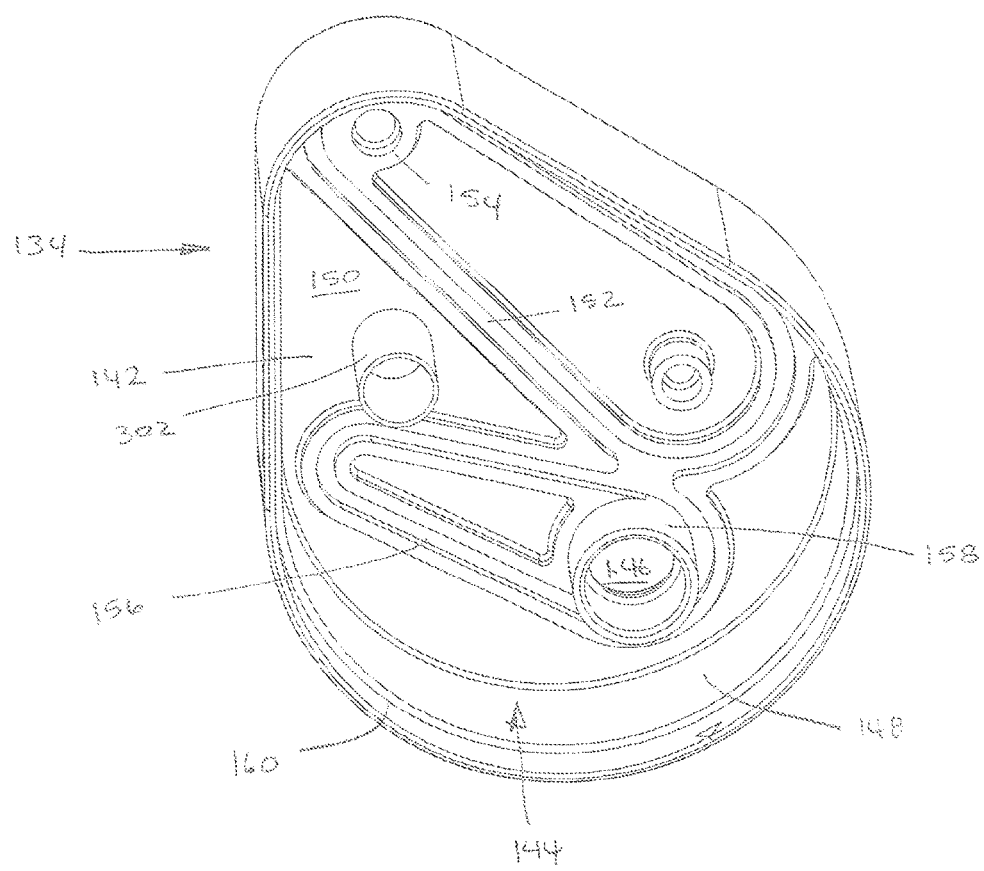
Figure 13:
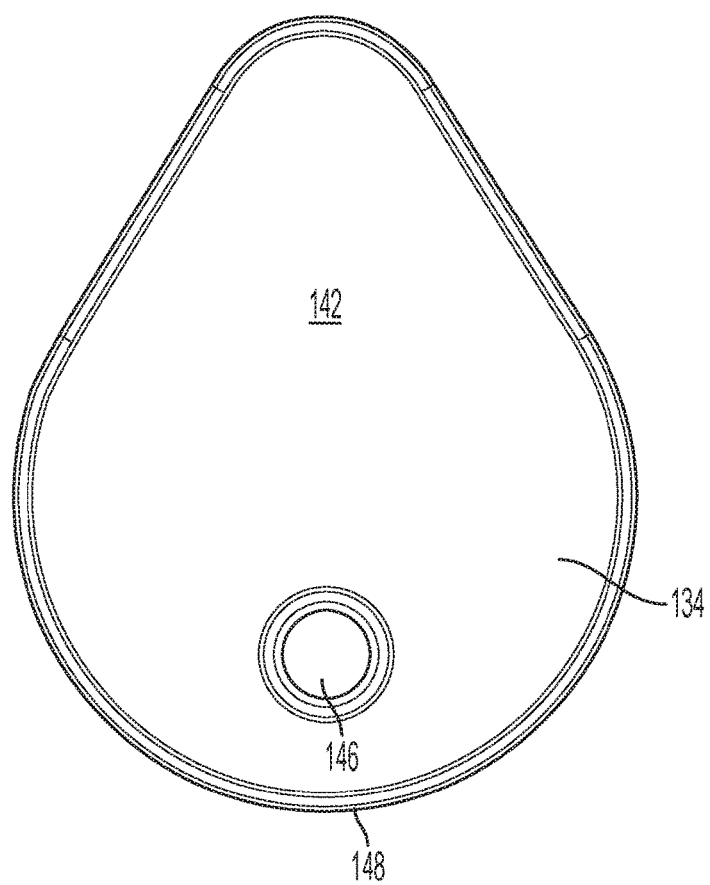
Figure 14:
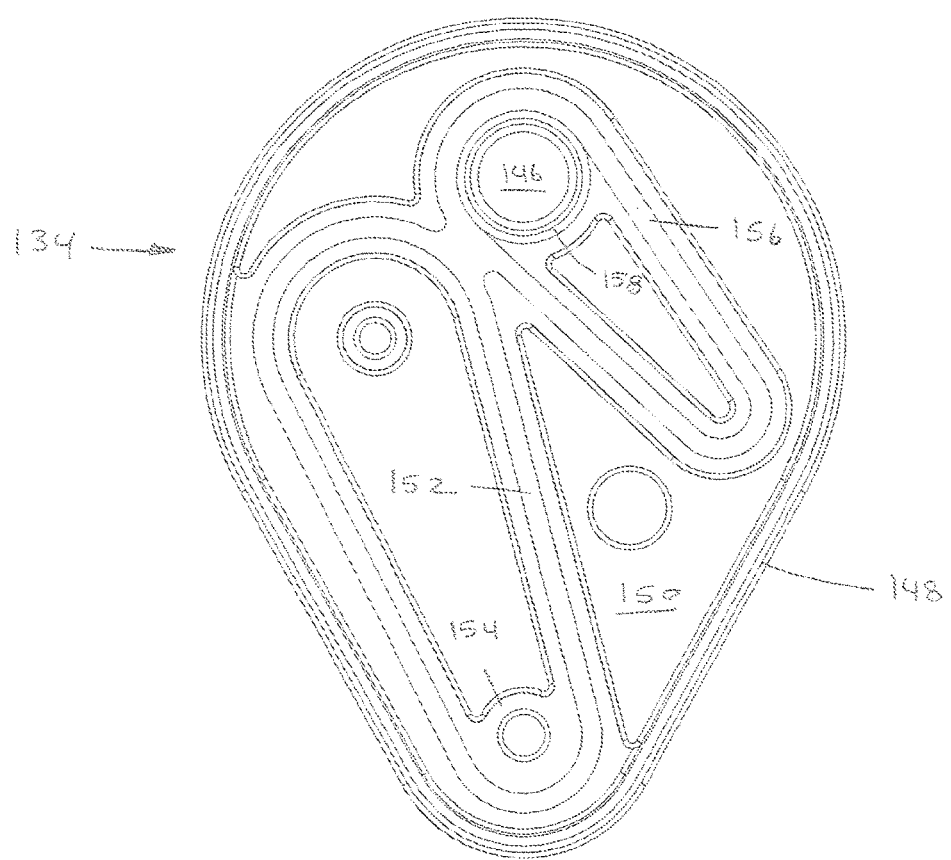
Figure 15:
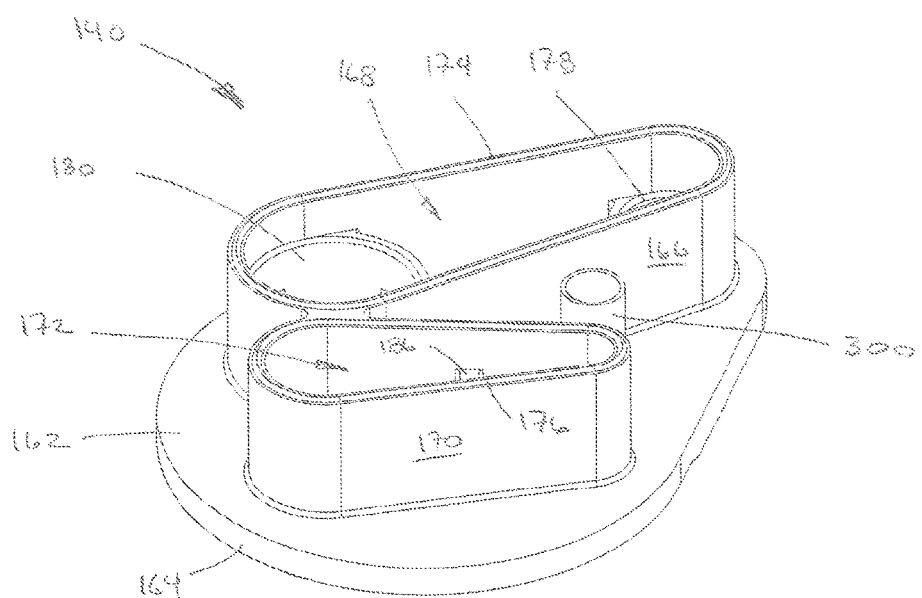
Figure 16:
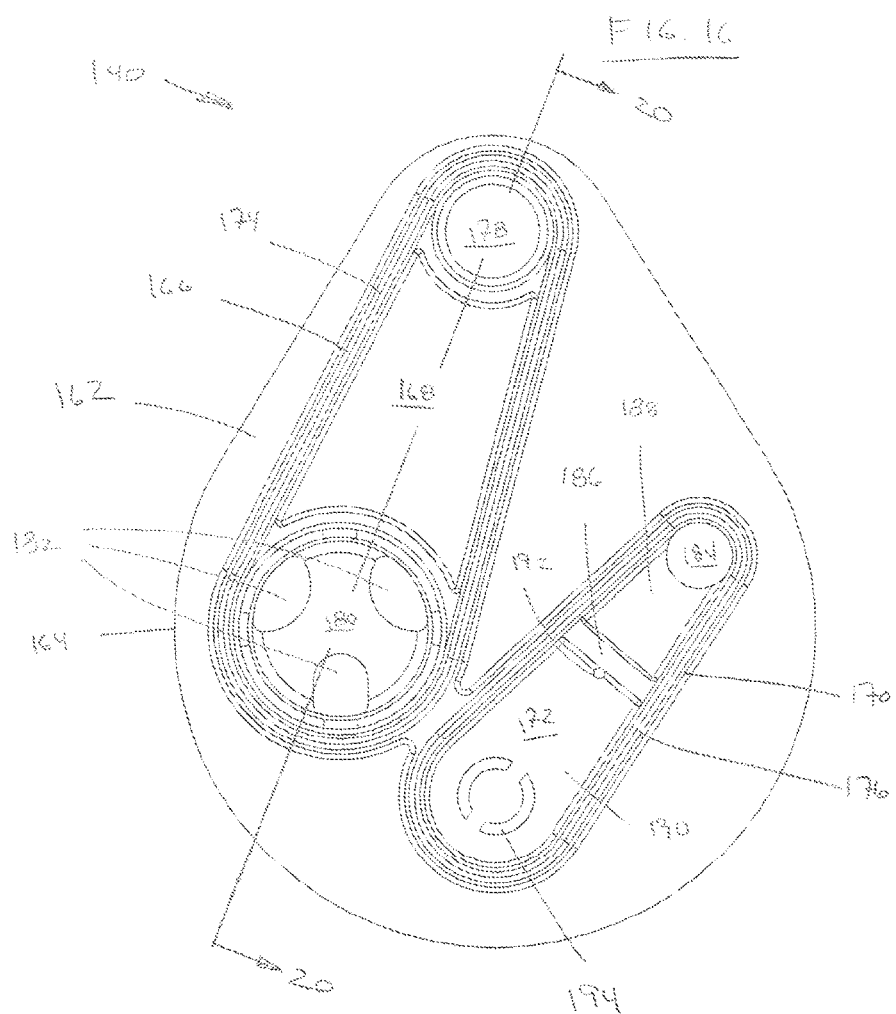
Figure 17:
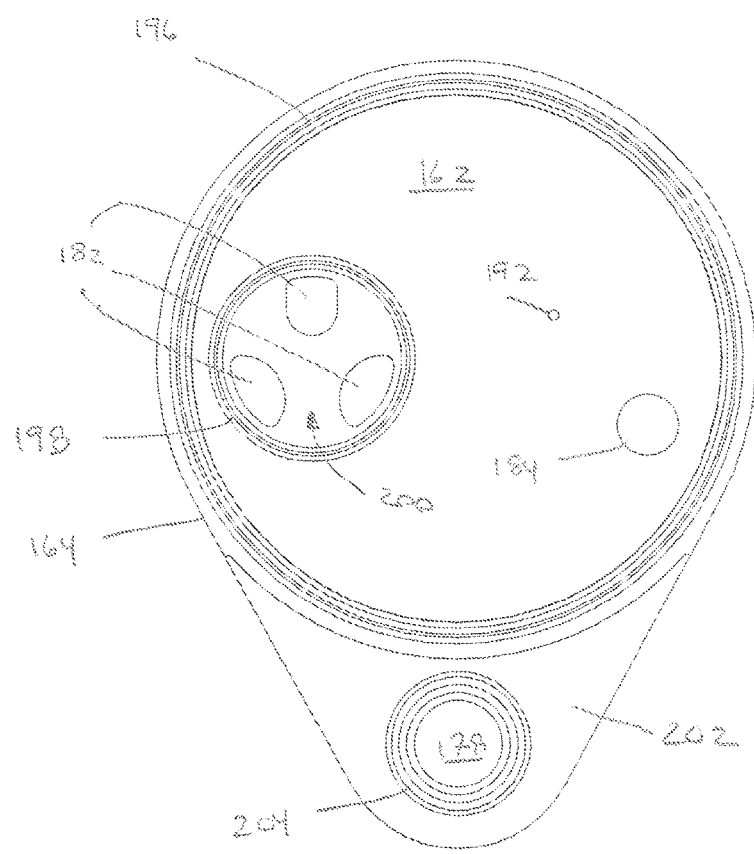
Figure 18:
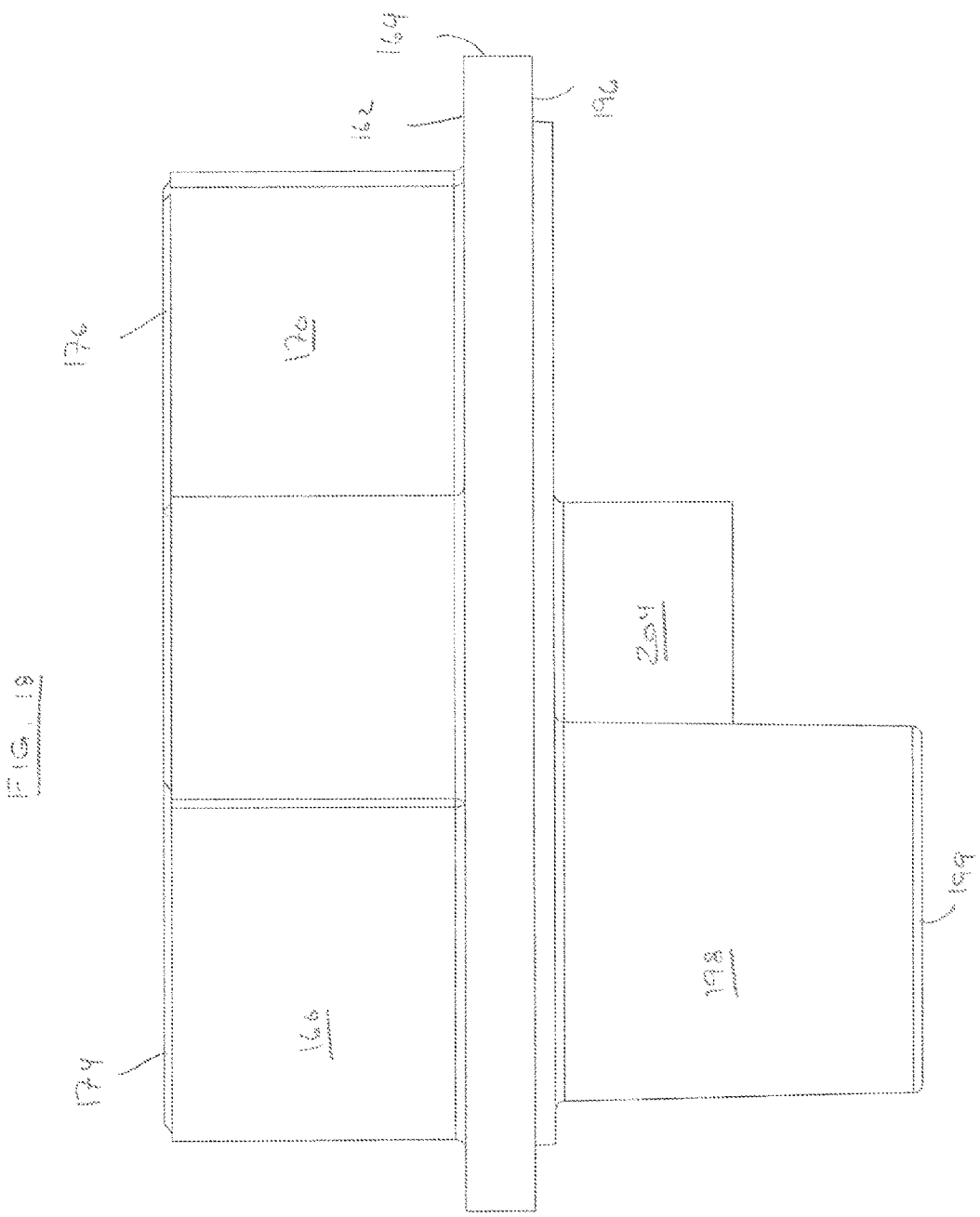
Figure 19:
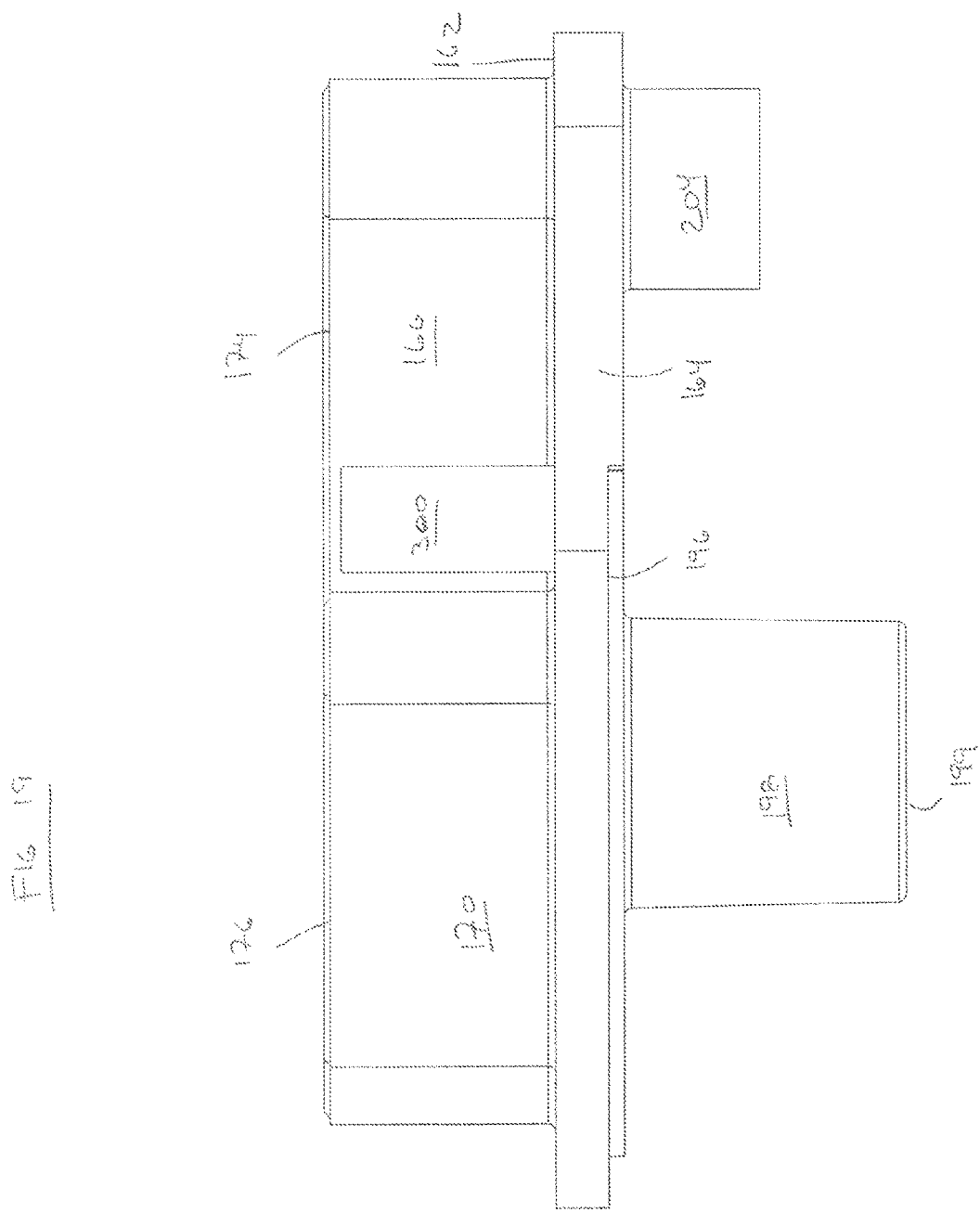
Figure 20:
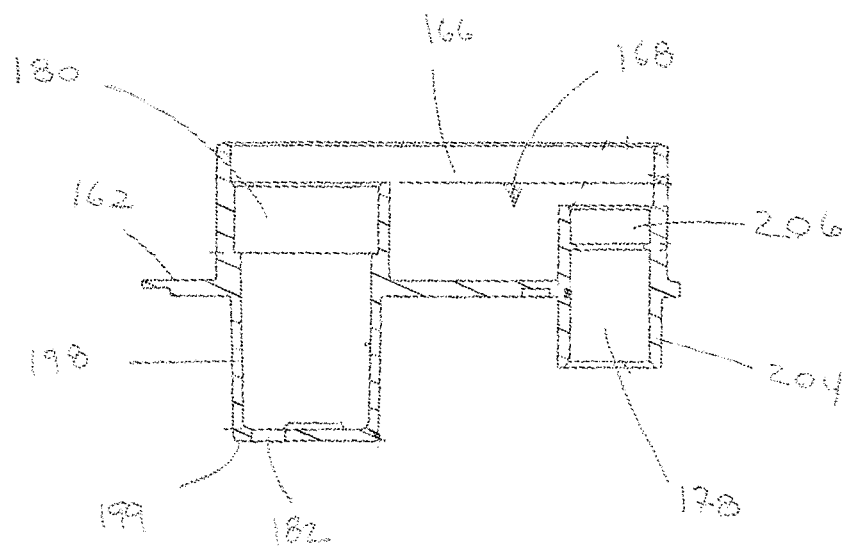
Figure 21:
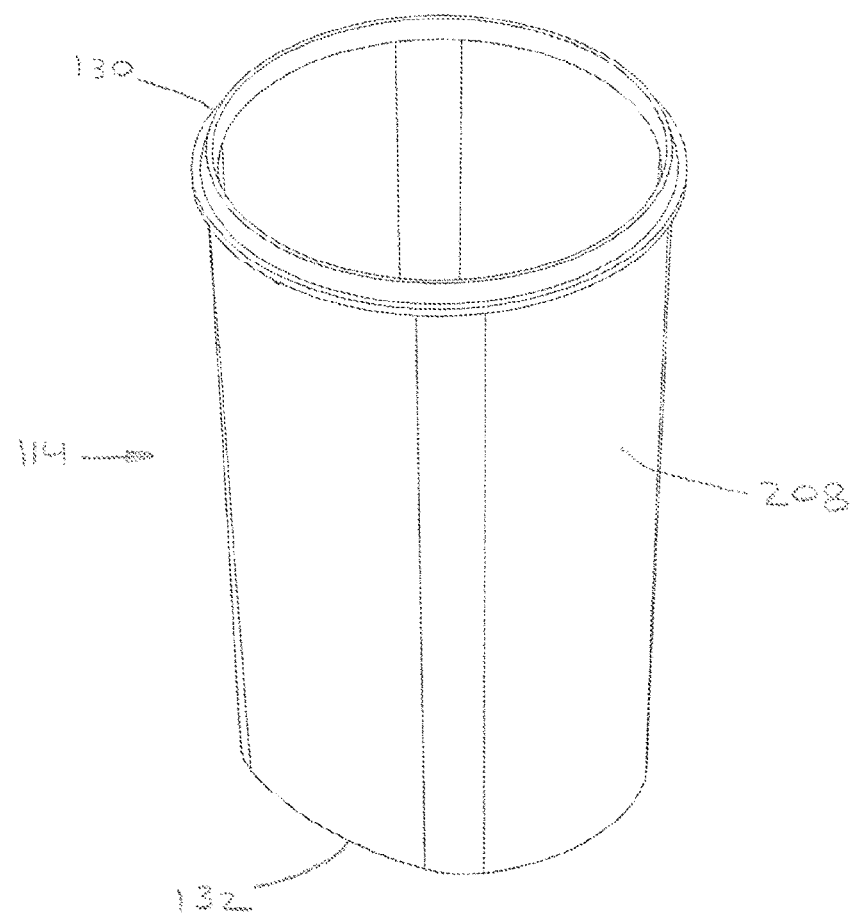
Figure 22:
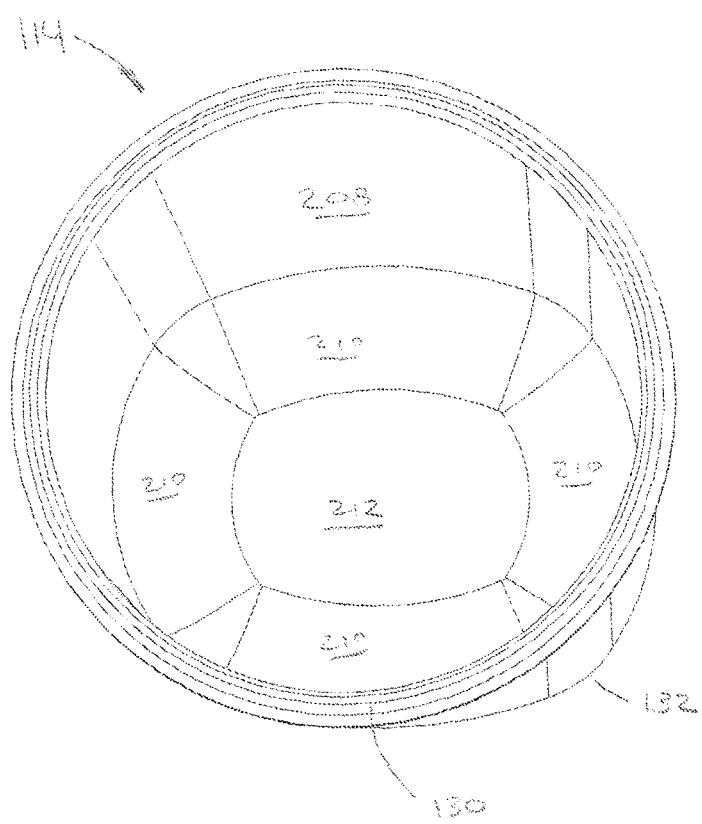
Figure 23:
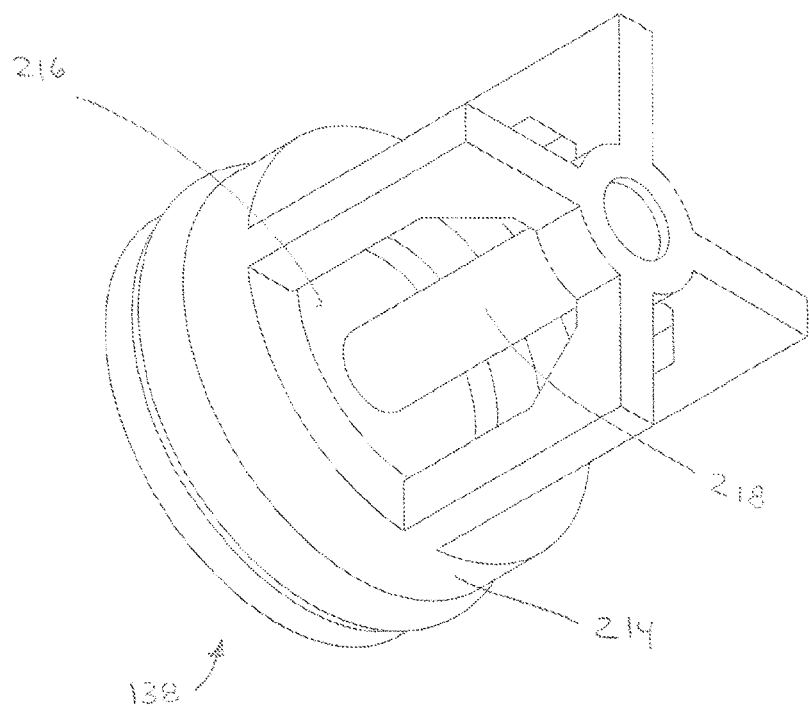
Figure 24:
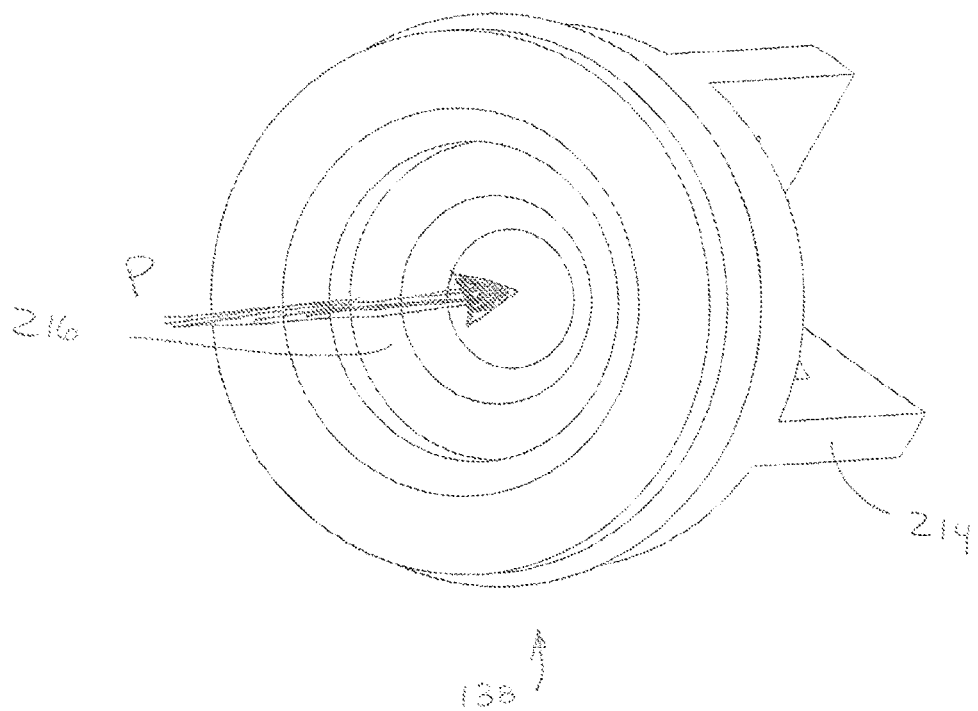
Figure 25:
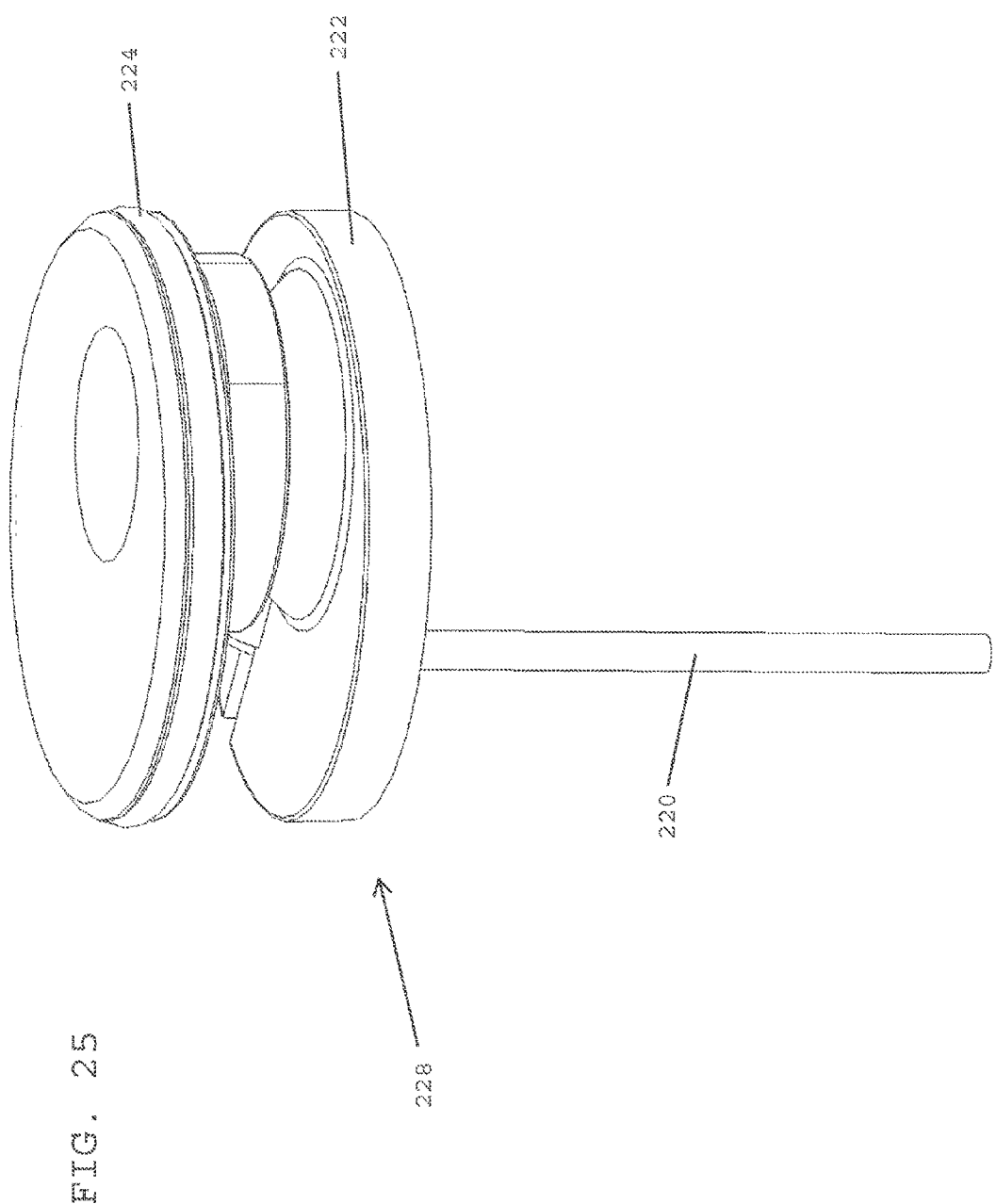
Figure 26:
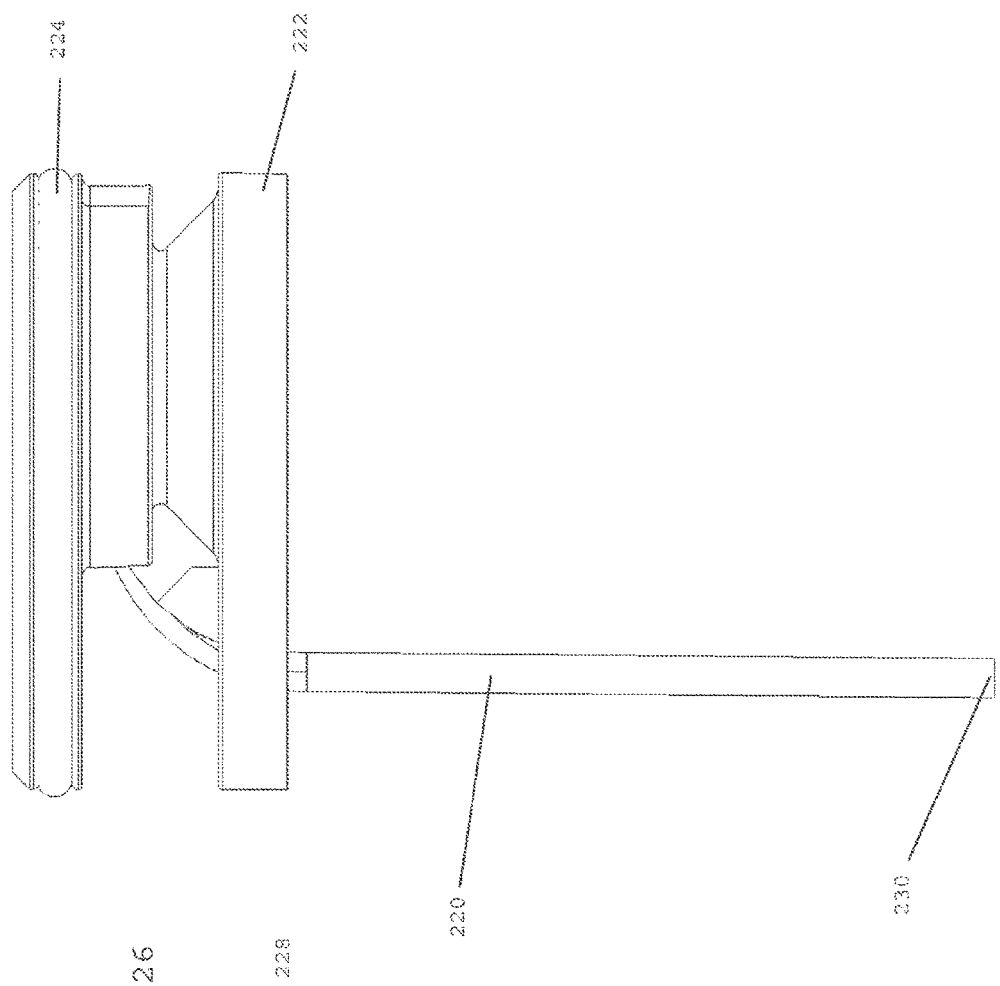
Figure 27:
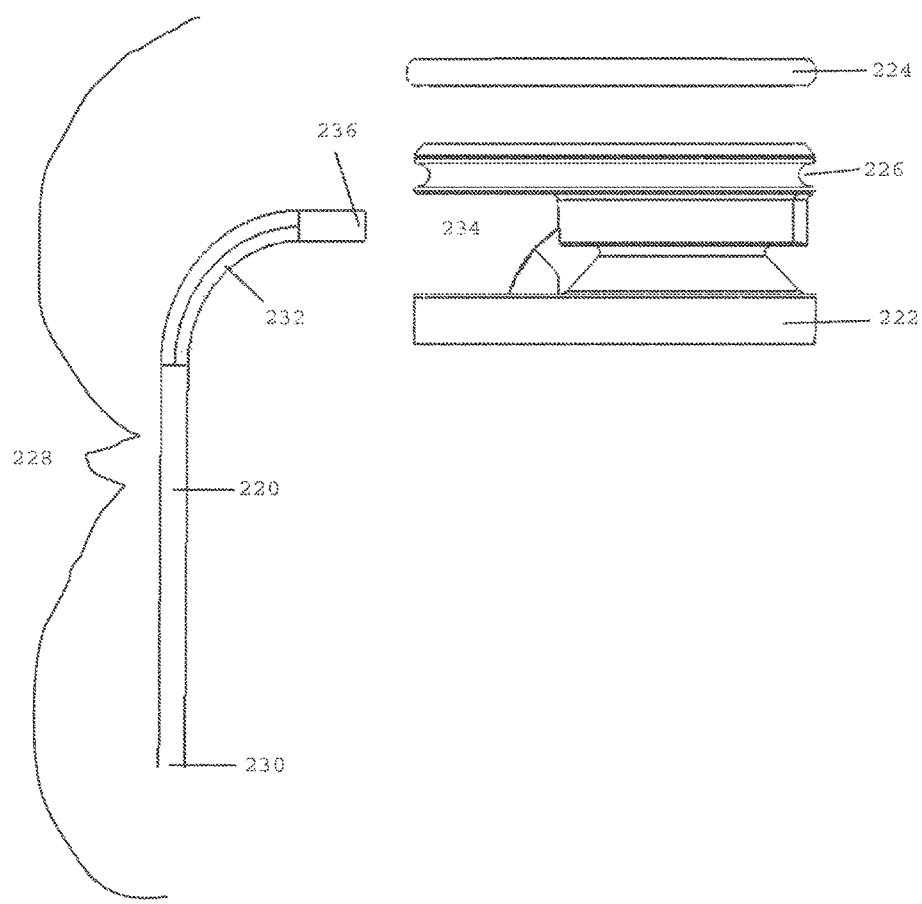

In FIGS. 1 to 4, a diffusion device 100 includes a housing 102 with a removable liquid cartridge 104 and a cover 106 enclosing both the housing 102 and the cartridge 104. One or more operational controls 108 or status indicators of housing 102 may be externally accessible and/or visible through a portion of cover 106. Alternatively, controls or status indicators 108 may be fully enclosed under cover 106 so that a smooth exterior image of device 100 is maintained. A outlet or opening 110 is provided in cover 106 to permit a diffused liquid stream from within cartridge 104 to be released into the atmosphere about device 100. A recess 112 may be provided in housing 102 to receive cartridge 104. When inserted in recess 112 as shown in FIGS. 3 and 4, cartridge 104 engages an outlet of the source of compressed gas within housing 102 and directs the gas through cartridge 104 as described below. The gas used to drive the diffusion of material by device 100 may be any of a variety of inert gases. As shown, device 100 may include an integral air compressor utilizing normal room air to drive the diffusion. However, other gases such as but not limited to nitrogen, carbon dioxide, or other similar atmospheric gases might be used. It may also be desirable to use a gas which reacts with the liquid to be diffused, such as but not limited to oxygen and other non-inert gases. Also, device 100 might utilize, for example but not limited to, an on-board compressor, an on-board source of compressed gas such as a pressurized reservoir, or may be connected to an external source of compressed gas.

Within the present disclosure, the terms atomize and diffuse are used in their various forms interchangeably. They are intended to refer to generally the same action, that being the dispersion of liquid into very small particle sizes (preferably but not limited to one micron or less in size) and releasing the particles into the atmosphere of a generally enclosed space. This particle size helps ensure that that the liquid to be dispersed remains airborne long enough to effectively treat the space.

A conventional approach to providing this small particle size is to incorporate a dispersion or gas-liquid mixing location adjacent an expansion chamber, which may include one or more baffles. The mixed gas and liquid combination may contain particles of greater than desirable size. Allowing this mix to remain resident within the expansion chamber prior to release into the treated space will allow the larger particles to precipitate out of the mix. Intermediate bulkheads or walls that a flow of the gas and liquid mix impinge upon may also assist in the collection of these larger particles and leave only the desired predominantly smaller sized particle to be released. This expansion chamber could be maintained at a positive pressure with respect to the atmospheric pressure within the space to be treated, so that the gas and liquid mix will be injected from the device into the space. Alternatively, the expansion chamber may generally be maintained at the atmospheric pressure of the space to be treated with the flow of gas through the chamber providing the impetus for movement of the gas and liquid mix from the device into the space to be treated. It may also be possible to have the pressure within the expansion chamber at a pressure lower than that of the treated space which may aid in the mixing or dispersion of the diffused liquid within the atmosphere within the space.

Within the context of this disclosure, diffusion also generally refers to a process or method of dispersing a liquid without destroying the integrity of the liquid compound. While some degree of reactivity between the gas and the liquid may be desirable, diffusion generally does not change the nature of the liquid, unlike heating or the application of electrical energy into the liquid to diffuse the liquid.

Device 100 may used to provide or introduce a pleasant or soothing scent (or some other type of liquid that may be used as an airborne treatment or compound) into the air space of a room or other enclosed space. The particular liquid to be dispensed by device 100 is contained within replaceable cartridge 104. Other possible types of liquids that may be dispersed by device 100 or similarly configured devices may include decontamination agents, insecticides, insect repellents, and many different types of liquids that may be desirably dispersed within an enclosed space. The present disclosure is not limited to a particular type or nature of liquid to be dispersed, but is intended to encompass any desirable airborne liquid treatments that are preferably dispersed within an enclosed space to be effective. The term enclosed space, as used herein, refers to any volume of space within which the atmospheric turnover is sufficiently slow to permit the dispersed liquid to have its desired effect within the space. Larger spaces, such as concert halls, casinos, lobbies, etc, may have one or more openings into the space and still have the desired characteristics to permit treatment with a diffused liquid. Other spaces may be preferably fully enclosed to permit treatment by the selected liquid. In other cases, the liquid used for treatment may preferably be used in a sealed space for maximum effectiveness or for safety reasons. Within the scope of the present disclosure, it is not intended to limit the nature, size or configuration of the space to be treated except as may be appropriate for the liquid used to treat the space and the nature of treatment within the space that is desired.

It is also anticipated that some of the compounds or materials that might be diffused into the space could be stored in a solid form and only dissolved or reduced to a liquid form immediately prior to diffusion. Storage as a solid may provide greater compound stability during transportation or storage, or may provide a greater shelf life for cartridges for use with diffusion devices of the present disclosure.

A source of compressed gas is provided within housing 102, such as a small air compressor or pump, an internal reservoir, or a connection to an external source of compressed gas. Controls 108 may be configured to provided to permit adjustment of the timing and force of compressed gas or air generated by the pump or compressor within housing 102 and directed into cartridge 104. Within cartridge 104, the compressed gas is directed to atomize the liquid within the cartridge and to aid in the dispersion of the atomized liquid from device 100 and into the air space to be treated.

As taught by conventional liquid diffusion devices, it may be desirable to have an indirect route from the point of actual atomization of the liquid within device 100 and the outlet through which a portion of the atomized particles exit from device 100. As will be described below, cartridge 104 provides an atomization zone where liquid from the cartridge and compressed gas from the housing meet and are mixed. In addition, cartridge 104 may also provide an expansion chamber within the cartridge where the atomized liquid is retained until a portion of the atomized liquid is allowed to leave device 100 through opening 110. Cartridge 104 may combine storage of the liquid to be diffused, an atomization structure to transform the liquid into an airborne concentration, an expansion chamber, and a path to outlet. These features are discussed in further detail below. Cartridges according to the present disclosure may also be used with conventional expansion chambers which are external to the cartridge to further aid in the separation of particle sizes and permit only desirably small particles to be allowed into the space to be treated.

Referring now to FIGS. 5 and 6, cartridge 104 includes a reservoir 114 within which is a liquid 116 that is to be diffused by device 100. Liquid 116 preferably does not fill all of a volume of reservoir 114 and defines a fluid level 118 that is offset from a diffusion head 122 mounted to reservoir 114. Above fluid level 118 and beneath diffusion head 122 is a generally open head space 120. Diffusion head 122 includes an outlet 124 for atomized liquid from within head space 120 to exit cartridge 106 and then pass through opening 110 of cover 106. An portion 126 of diffusion head 122 extends beyond a footprint of reservoir 114 and engages the source of compressed gas when cartridge 104 is positioned within recess 112 of housing 102.

FIG. 7 shows a bottom view of cartridge 104 with a gas inlet 128 on a lower surface of diffusion head 122 under extension 126. Reservoir 114 includes an upper edge 130 which engages diffusion head 122. Upper edge 130 is preferably round as is a mating rim on an under side of diffusion head 122 to aid in the assembly of cartridge 104. A rounded interface between diffusion head 122 and reservoir 114 will provide different options for how the two pieces may be fitted to each other during production and how the junction between the two pieces may be sealed to prevent leakage or contamination of liquid 116. One method of connecting diffusion head 122 and reservoir 114 may be by spin welding, though other suitable methods or techniques of joining and bonding the two parts may also be used within the scope of the present disclosure. A tapered body between upper edge 130 and a lower edge 132 of reservoir 114 may aid in positioning and vertical insertion of cartridge within recess 112 of housing 102. Such a tapered shape may also cooperate with an internal shape of a bottom of reservoir 114 to aid in efficient use of all liquid 116 within the reservoir.

FIGS. 8 to 10 illustrate some of the components comprising diffusion head 122, including a top cap 134 to which a label 136 may be attached to an upper portion. A pair of one way flow devices 138 may be included within diffusion head 122, and a baffle 140 may be mounted to top cap 134. One of the one way flow devices 138 may be mounted to baffle 140 adjacent inlet 128 and a second one way flow device 138 may be mounted to baffle 140 adjacent outlet 124. The function of one way flow devices 138 will described further below.

FIGS. 11 to 14 illustrate top cap 134 with a top wall 142 and an lower cavity 144 defined by top surface 142 and a circumferential wall 148. An opening 146 is provided for atomized liquid to pass through. Within cavity 144 along a bottom surface 150 of top wall 142 are a first continuous groove 152 and a second continuous groove 156. These continuous grooves 152 and 156 define regular shapes that match up with upward extending walls of baffle 140 and aid in sealing chambers or cavities for directing gas from inlet 128 into reservoir 114 and from reservoir 114 to outlet 124. Within first groove 152 may be a molded feature 154 to aid the positioning of one way flow device 138 to control the flow of gas from inlet 128 into cartridge 104. Opening 146 is positioned within groove 156 and may include a circumferential wall extending around the opening and extending from bottom surface 150. Along an inner surface of wall 148 a ledge 160 may be included to aid in connecting top cap 134 to baffle 140 to assembly diffusion head 122.

Referring now to FIGS. 15 to 20, baffle 140 includes a lower plate 162 with an outer mating edge 164 to engage a lower edge of wall 148 of top cap 134 and ledge 160. Extending upward from lower plate 162 are a first wall 166 defining an inlet cavity 168 and a second wall 170 defining an outlet cavity 172. An upper edge 174 of wall 166 is configured to engage groove 152 of top cap 134 and an upper edge 176 of wall 170 is configured to engage groove 156 of top cap 134.

Within inlet cavity 168 is an opening 178 for receiving and mounting one way flow device 138 to regulate gas flow into cartridge 104 and flow of liquid 116 out of cartridge 104. Also within cavity 168 is an recess 180 for mounting a venturi and tube assembly, shown below. One or more openings 182 are provided within recess 180 permitting passage of gas and/or liquid from cavity 168 into reservoir 114. Gas flow during operation of diffusion device 100 would generally be from inlet 128 through opening 178 into cavity 168 and then through recess 180 and openings 182 into reservoir 114.

Outlet cavity 172 includes an opening 184 for gas and atomized liquid to flow from head space 120 of reservoir 114 into the cavity. A transverse bulkhead 186 extends across cavity 172 and divides the cavity into a first chamber 188 and a second chamber 190. Bulkhead 186 does not extend to upper edge 176 so that the first and second chambers are in fluid communication with each other over bulkhead 186.

Bulkhead 186 may aid in the separation of undesirably large particles of airborne liquid from exiting cartridge 104 by providing additional space for such large particles to precipitate out of the gas and atomized liquid exiting through cavity 172. Any precipitate accumulating in chamber 188 may flow back into reservoir 114 through opening 178. Any precipitate accumulating in chamber 190 may flow back into reservoir 114 through a weep hole 192. Weep hole 192 may help prevent undesirable build up of liquid within chamber 190 that may interfere with smooth passage of gas and atomized liquid from opening 184 through cavity 172 and through outlet 124. Bulkhead 186 is preferably positioned close to the level of upper edge 176 to encourage precipitation of undesirable large particles and to discourage refilling of cartridge 104, as will be described below, and far enough below the level of upper edge 176 so as not unduly impede movement of the liquid and gas mix from the reservoir to the outlet.

A molded feature 194 may be included within cavity 172 to aid in positioning a one way flow device 138 adjacent to opening 124. This one way flow device would regulate the flow of gas and atomized liquid through opening 124 and prevent liquid 116 from escaping through opening 124.

Referring now to FIG. 17, on a lower surface of lower plate 162 is a round mating surface 196 sized and configured to mate within upper edge 130 of reservoir 114. By having a round mating surface, different techniques to sealing the baffle to the reservoir may be used, including spin welding, in addition to but not limited to gluing, meltbonding, ultrasonic welding and other known techniques.

Positioned about openings 182 and extending from lower plate 162 is a wall 198 defining an initial expansion chamber 200 for gas and atomized liquid being ejected into head space 120 from the venturi to be mounted within recess 180. Preferably, a lower extension 199 (shown in FIGS. 18 and 19) of wall 198 does not extend as far as liquid level 118 so that the atomized liquid from the venturi and expansion chamber 200 escape easily into head space 120. Openings 182 may be positioned adjacent lower extension 199 of wall 198.

An extension 202 of lower plate 162 extends beyond mating surface 196 and forms a lower portion of extension 126 of diffusion head 122. Extending from extension 202 is a wall 204 about inlet opening 178. Wall 204 may engage a mating feature within or adjacent to recess 112 of housing 102 to aid in the positioning of cartridge 104 into recess 112 and proper engagement of the source of compressed gas of housing 102. A recess or valve seat 206 (shown in FIG. 20) may be provided within opening 178 to permit proper seating of one way flow device 138 in the gas inlet.

Referring now FIGS. 21 and 22, reservoir 114 includes a side wall 208 extending between upper edge 130 and lower edge 132. Side wall 208 may taper or narrow as it transitions from edge 130 to edge 132. As shown, side wall 208 may also change shape at it transitions between the upper and lower edges. As shown, adjacent edge 130, side wall 208 defines a generally round shape while adjacent edge 132, side wall 208 defines a more ovalized shape. The choice of shape and taper of side wall 208 may be made for aesthetic reasons as well as to ensure that cartridge 104 is properly configured and positioned to engage and work with housing 102. A distinctive profile of side wall 208 may provide a quick visual indication that a particular cartridge is a proper mating cartridge for use with device 100.

As shown in FIG. 22, adjacent edge 132 an inner surface or surfaces 210 of side wall 208 may transition toward and define a smaller base 212 within reservoir 114. Such a smaller base will help to concentrate liquid 116 when the fluid level 118 lowered within reservoir 114. When cartridge 104 is almost fully depleted, and fluid level 118 is adjacent base 212, having a smaller base 212 may aid in ensuring that a tube (shown below) will deplete as much of liquid 116 as possible before cartridge 104 needs to be replaced.

FIGS. 23 and 24 illustrate prior art one way flow device 138, which may be a commercially available product. One way flow device 138 may include a fixed portion or cage 214 and movable portion or seal 216 movably mounted to cage 214 and biased toward a closed position by a spring member 218. To open one way flow device 138, pressure (illustrated as P in FIG. 24) may be exerted on seal 216 until the bias pressure of spring member 218 is overcome. When spring member 218 is overcome, seal 216 moves deeper into cage 214 and flow is permitted about seal 216 through cage 214. Spring member 218 may be a resilient member so that when pressure P is reduced to less than the bias pressure, spring member 218 moves seal 216 back into the closed position as shown in the FIGS. Pressure P may be applied to seal 216 by either direct physical contact or by a build up of fluid pressure.

As indicated above, one way flow devices 138 may be positioned within diffusion head 122 in both the inlet and outlet cavities of baffle 140. It is anticipated that one way flow device 138 will be inserted within seal 216 facing downward in seat 206 in opening 178. When cartridge 104 is placed within recess 112 of housing 102, opening 178 is connected to the source of pressurized gas. Gas pressure may be used to overcome spring member 218 and open one way flow device 138 and permit pressurized gas to enter cartridge 104. Alternatively, recess 112 may include a valve engaging member that extends into opening 178 and mechanically presses one way flow device 138 open.

It is anticipated that one way flow device 138 will be positioned within second chamber 190 of outlet cavity 172 beneath opening 146 with seal 216 facing upward. One way flow device 138 in this position would prevent contamination from entering inlet cavity 172 and also prevent liquid 116 from leaking through opening 146. Cover 106 may include a member inside the cover adjacent outlet 110 to engage and depress seal 216 downward when cover 106 is placed over housing 102 and cartridge 104.

The cooperation of one way flow devices 138 with housing 102 and cover 106 permits cartridge 104 to be configured with a secure seal against contamination or leakage of liquid 116 during transportation and storage of cartridges 104 prior to use. These seals do not require direct intervention of a user to prepare cartridge 104 for use with device 100. Preferably, seals 216 of one way flow device 138 are resilient and durable, so that cartridge 104 may be removed from housing 102 prior to being fully depleted of liquid 116 and stored for reuse. During partial use storage, one way flow devices 138 would return to the closed position and protect against leaks and contamination. The cartridge could then be reused until fully depleted.

Such an arrangement of one way flow devices would permit cartridges to be replaced whenever a new scent or air treatment is desired required, without wasting any unused portion of a removed cartridge. Such an arrangement of one way flow devices 138, in cooperation with the configuration of outlet cavity 172 with intermediate transverse bulkhead 186, may also prevent or render inefficient attempts to refill cartridges 104 or to introduce undesirable elements into cartridge 104. A one way flow device 138 may be installed atop feature 194 in second chamber 190, with seal 216 facing upward. The combination of one way flow device 138 and bulkhead 186 makes it difficult to insert a tube or conduit through opening 126, through one way flow device 138, up and over bulkhead 186 and then through opening 184 into reservoir 114. Merely depressing seal 216 of one way flow device 138 will permit a person to only charge second chamber 190 with the liquid or material to be introduced into reservoir 114. Cartridge 104 could then be tilted to empty second chamber into the first chamber and have it drain through opening 184. Weep hole 192 is sized to permit small amounts (drops) of precipitated liquid to drain into reservoir 114 and is preferably not large enough to permit larger amounts of liquid to be quickly introduced into reservoir 114. It is also anticipated that a flapper valve or similar arrangement might be placed between a top edge of bulkhead 186 and bottom surface 150 of top wall 142. Such a flapper or other valve might be biased to allow atomized liquid and gas to pass from opening 184 to opening 126, but to close off the space between bulkhead 186 and bottom surface 150 of top wall 142 when cartridge 104 is tilted to encourage liquid to flow over bulkhead 186 in the opposite direction.

Referring now to FIGS. 25 to 30, a venturi and tube assembly 228 for use within diffusion head 122 may include a tube 220, a venturi head 222 and a o-ring or other seal member 224 seated within a seat 226. Assembly 228 is sized to fit within recess 180 with a first end 230 of tube 220 extending one of the openings 182 into reservoir 114 and below liquid level 118, preferably to a position adjacent base 212. Seal member 224 is sized and configured to closely engage an inner surface of recess 180. A curved transition 232 of tube 220 extends to a second end 236. End 236 is positioned within head 222 which may also provide a curved support 234 for transition 232.

Figure 28:
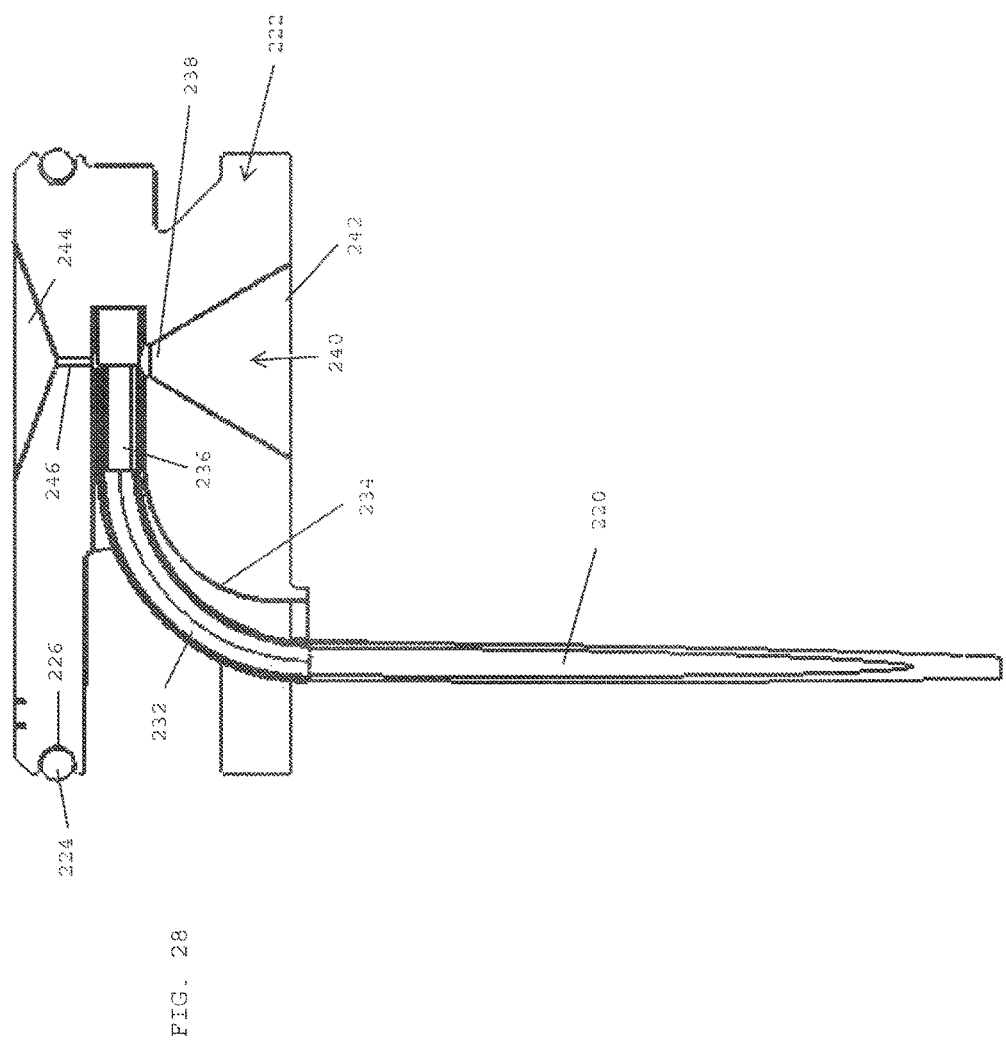
Figure 29:
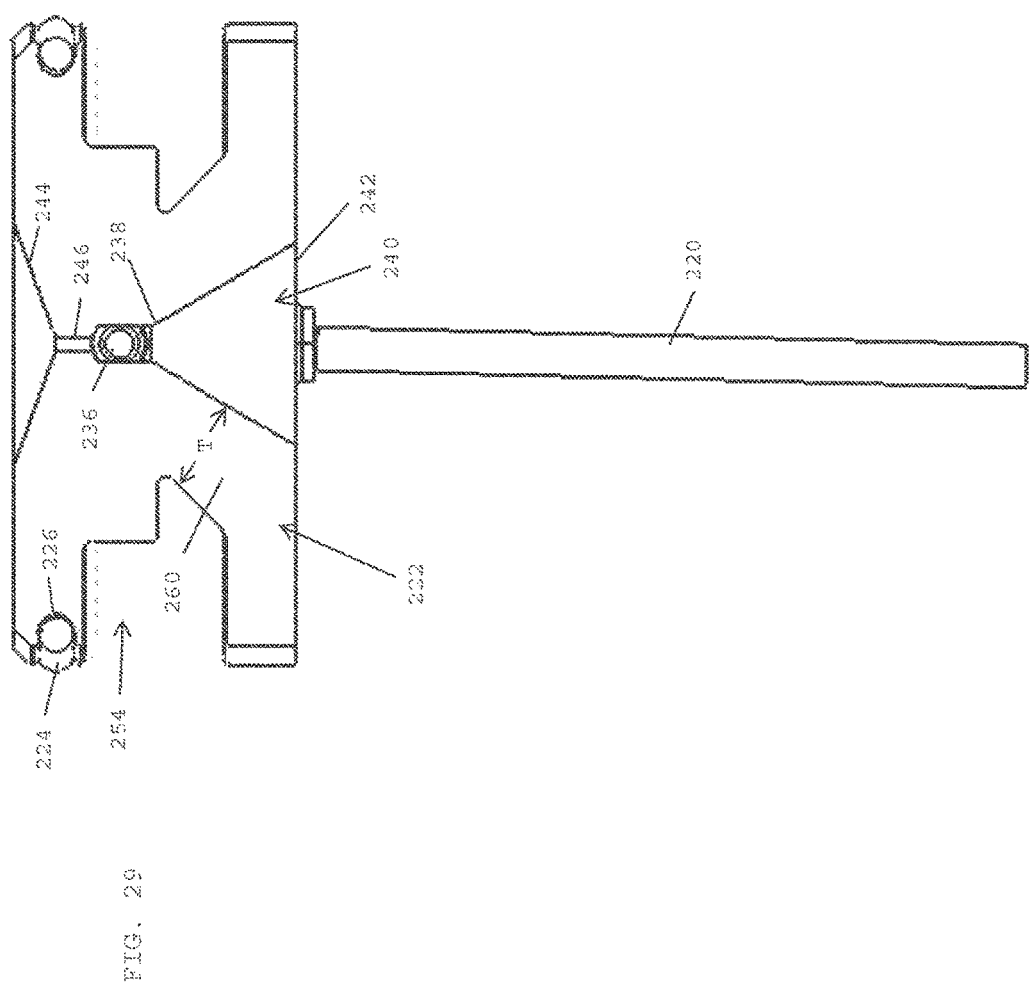
Figure 30:
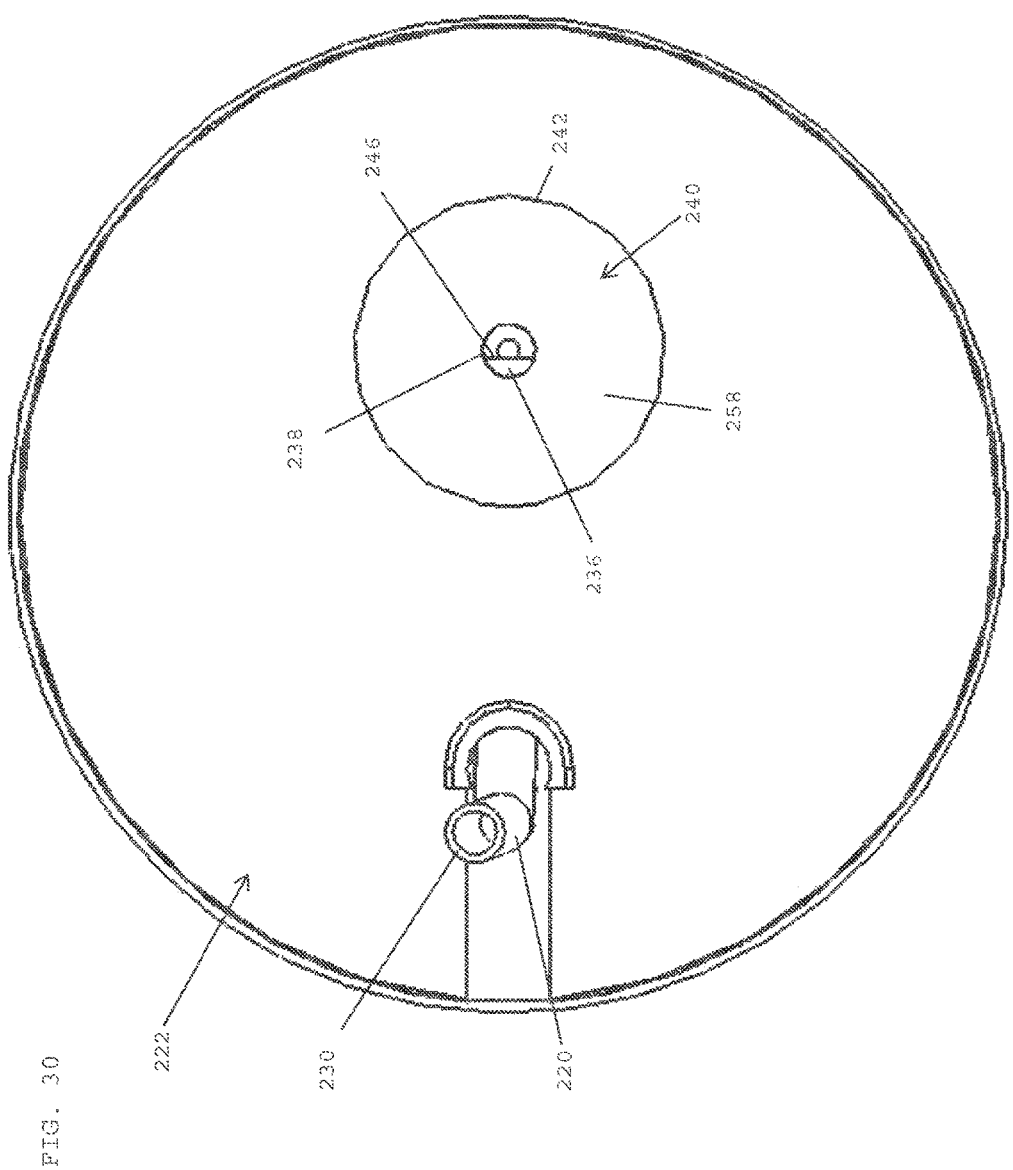

Referring now to FIGS. 28 and 29, second end 236 of tube 220 is positioned adjacent a narrow end 238 of a venturi 240. Venturi 240 extends generally conically from narrow end 238 to a wide end 242, defining an atomizing chamber directed towards openings 182 of baffle 140. An upper gas entry 244 is provided that would be exposed to inlet cavity 168 of baffle 140 and thus exposed to compressed or pressurized gas from housing 102. Gas entry 244 may also be a tapered or venturi shape to aid in the transitioning of gas flow into a gas passage 246 into narrow end 238 of venturi 240. The shape of gas entry 244 may be configured based characteristics of the gas flow from housing 102, the geometry of inlet cavity 168 and the volume and speed of gas required to effectively draw liquid 116 up tube 220 and atomize liquid 116 in venturi 240.

Gas passage 246 directs the gas into narrow end 238 of venturi 240. The gas flow in narrow end 238 creates a low pressure environment adjacent second end 236 of tube 220. This vacuum draws liquid 116 up tube 220 and into narrow end 238. High velocity gas and liquid 116 mix in venturi 240 as they pass from narrow end 238 to wide end 242. Leaving venturi 240, the mixed gas and liquid pass through openings 182 and into head space 120 of reservoir 114. This may also pressurize the gas within head space 120.

The flow of gas and diffused liquid into head space 120 will urge gas and diffused liquid to flow toward the only exit from head space 120, which is through opening 184 and into outlet cavity 172. Gas flowing through opening 184 will also transport any atomized liquid suspended in the gas into outlet cavity 172. While the gas and suspended liquid are within head space 120, larger, less desirable liquid particles atomized in the gas should precipitate back into liquid 116. To pass from first chamber 188 into second chamber 190, the gas/liquid mixture must pass over bulkhead 186. While the gas/liquid mixture passes through first chamber 188, additional large liquid particles may precipitate out and drain back into reservoir 114.

To exit second chamber 190, the gas/liquid mixture must pass about an opened one way flow device 138 and exit through opening 146. Any additional liquid particles precipitating within second chamber 190 may drain back into reservoir 114 through weep hole 192. Thus, by the time a gas/liquid mixture exits from cartridge 104, there has been some amount of time during residency in the head space and passage through the two chambers of outlet cavity 172 to permit undesirably large liquid particles or droplets to precipitate from the mixture and be returned to reservoir 114 for later atomization and dispersion.

Figure 31:
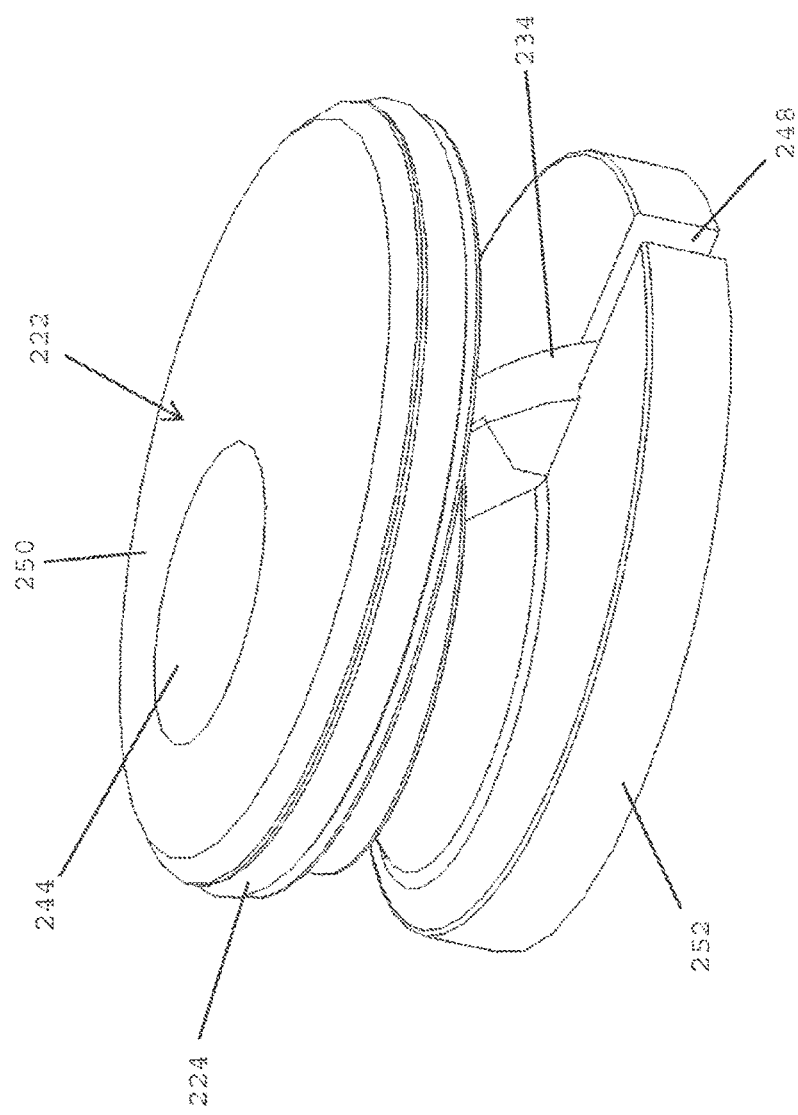
Figure 32:
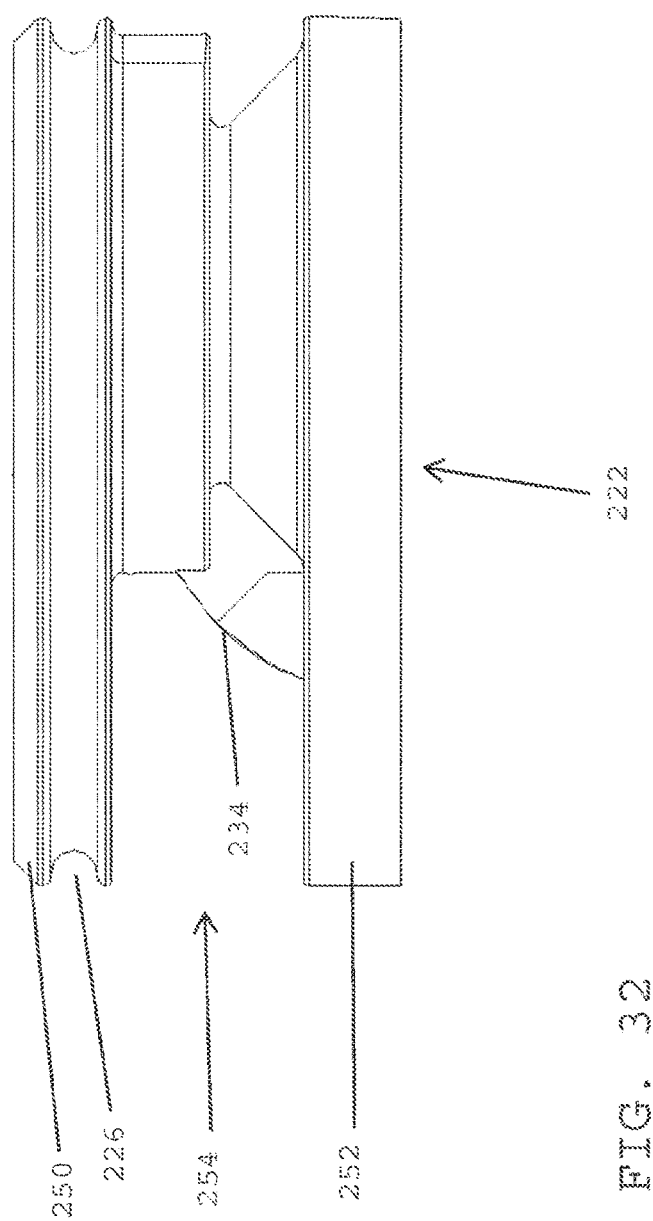
Figure 33:
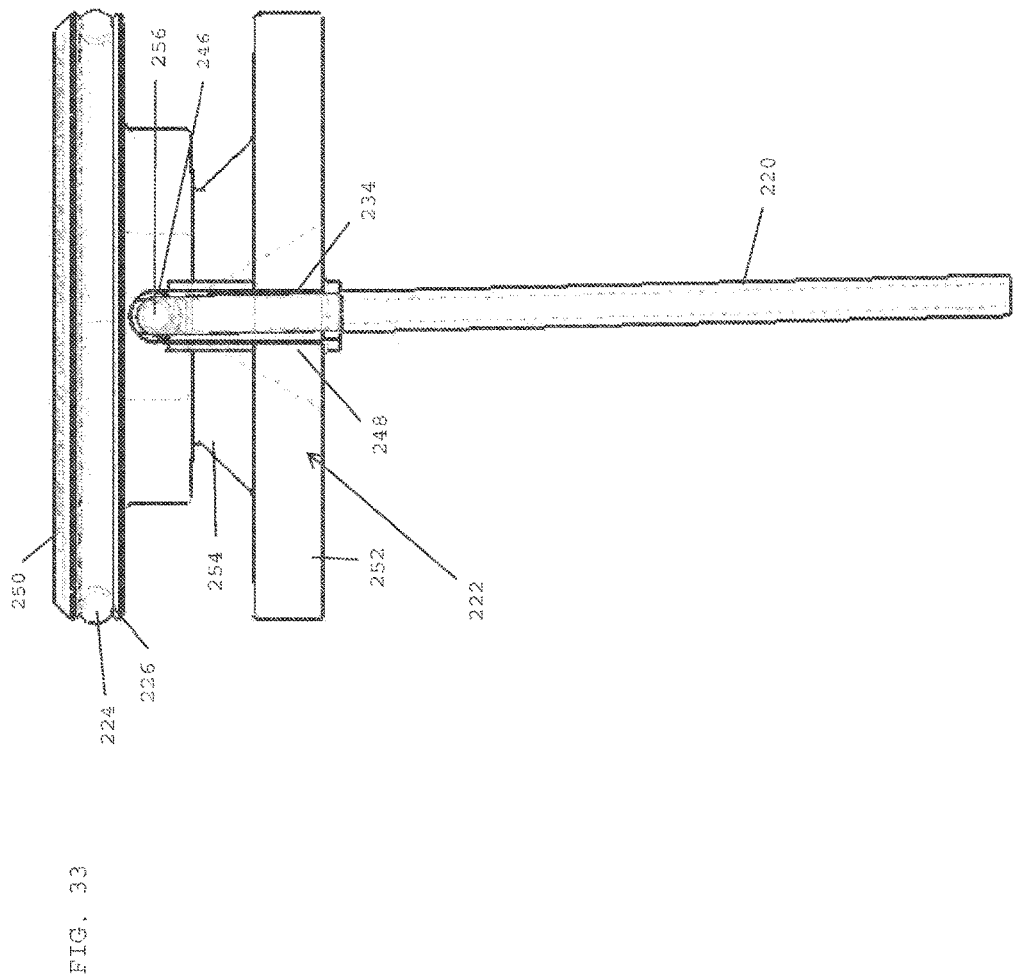

Referring now to FIGS. 31 to 33, head 222 may be molded as a unitary piece of material, such as a suitable plastic or polymeric material. As it is typically easier to control dimensions and thicknesses with smaller amounts of molded material, head 22 may be configured with an upper seal portion 250 including seat 226 and gas entry 244, a lower portion 252 including wide end 242 of venturi 240 and an intermediate portion 254. For a given size and specification of compressed gas source in housing 102, the speed and volume of gas passing through venturi 240 will be determined by the size of gas passage 246 and narrow end 238. Molding head 222 as a generally uniformly sized block between upper and lower portions could include too much material in the molding process, making it difficult to control the size and shape of gas passage 246 and narrow end 238. As shown in FIG. 29, a thickness T of a wall 260 of intermediate portion 254 may be selected based on the characteristics of the material used to form head 222 to help ensure that the shape of venturi 240 meets a desired shape for efficient operation of diffusion cartridge 104.

Intermediate portion 254 may also include a liquid entry such as an opening 256 permitting insertion of second end 236 of tube 220 to a position adjacent narrow end 238 of venturi 240 and gas passage 246. Lower portion 252 may include a slot 248 to permit insertion of tube 220 during assembly of venturi and tube assembly 228. Flow of gas through gas entry 244 and into narrow end 238 of venturi 240 creates a lower pressure condition adjacent second end 236 of tube 220. The lowered pressure urges liquid to be drawn through tube 220 into venturi 240 where it can mix with gas entering through gas entry 244. The mixing of gas and liquid within venturi 240 causes the liquid to be atomized into smaller airborne liquid particles. The gas and liquid particles are urged through venturi 240 by the pressure of the gas and exit through wide end 242 of venturi 240.

A surface 258 of venturi 240 extending between narrow end 238 and wide end 242 may include a coating or molded texture. Such a coating or texture may enhance the removal or precipitation of larger than desired atomized particles or droplets of liquid prior to release of the atomized liquid from cartridge 104 into the space to be treated.

During operation of device 100, it is not uncommon for some very small contaminants within the pressurized gas or liquid 116 to build up within gas passage 246 or venturi 240. Such a buildup may significantly degrade the ability of device 100 to treat the air as desired. Due to the size of the passages that may be blocked or occluded, it may not be feasible or desirable to clean or permit a user to remove the buildup. It is anticipated that many portions of cartridge 104 will be made from molded or formed plastic or polymeric materials. Such materials may be too soft to effectively clean and may be so damaged during the cleaning process that the function or performance of device 100 or cartridge 104 may be irrevocably degraded.

In addition, if users are successful in refilling cartridges 104 with the same or different liquids 116, users may be attempting to use the cartridges beyond a point where the buildup of material has fully compromised function of device 100.

To address this issue, it is anticipated that head 222 may be molded or formed from a material with known degradation characteristics when exposed to liquid 116, the gas used to drive the diffusion, or the pressure of the gas passing through the head. The degradation of head 222 may be matched with the expected life of the liquid in the cartridge and normal operation of device 100. Head 222 may also be made of a bio-degradable material which may have the known degradation characteristics. It is also anticipated that all of cartridge 104 may be made of a biodegradable material, as it may be desirable that the cartridge is configured to be used only one time before being discarded. It is also anticipated that cartridge 104 could be configured to be returned to a manufacturer or other entity after its planned use to have the cartridge disassembled, cleaned, any worn or damaged parts replaced and then refilled and resealed for use.

When changing a scent or treatment liquid in a conventional diffusion device 100, it would not be unknown for some amount of the prior liquid to remain in the tube, the venturi, the mixing chamber or other areas of the outlet path. These prior liquids would essentially contaminate the new scent or treatment liquid desired until they are purged from the outlet path through either cleaning or continued operation of the system. Having cartridges 104 with all elements of the tube, mixing zones, and outlet path contained in a single removable unit, changes to the scent or air treatment dispensed by device 100 can be accomplished without any undesirable cross-contamination from prior scents or treatments. Prevention of such possible cross-contamination is especially desirable or required in settings such as treatment of medical facilities where a high degree of cleanliness is essential, or when delivering liquids which may react with each other.

In the present disclosure, the openings of the housing and/or the cartridge have permitted the atomized liquid from with the cartridge to flow directly into a space to be treated. However, the openings could direct the diffused liquid into an air transport or distribution system instead. The air transport system might include ductwork or other avenues that would permit the diffused liquid to the dispersed into a remotely located space or a plurality of remotely located spaces. Thus, cartridge 104 could be used to diffuse and disperse liquid throughout an entire building, for example, through the existing HVAC conduits.

It is also anticipated that cartridge 104 might be adapted to mount directly to a fitting on a conduit or source of compressed gas without the need for mounting within or as part of a housing. Such a fitting might permit cartridge 104 to be positioned to treat air within a single enclosed space or may be used to treat air flowing through a air transport system and treat a plurality of spaces. Alternatively, a plurality of cartridges might be used to treat individually spaces but may be linked to the same gas source. The source of compressed gas could then be controlled centrally for all of the spaces treated without the need for or provision of local controls for each treated space. Or each space could have a valve for controlling the flow of gas through the cartridge and thus the strength or intensity of the treatment within a particular space. Such local control valves could be then permit the same or similar cartridges to be used in conjunction with a common gas source to treat a plurality of different sized or configured spaces.

Figure 34:
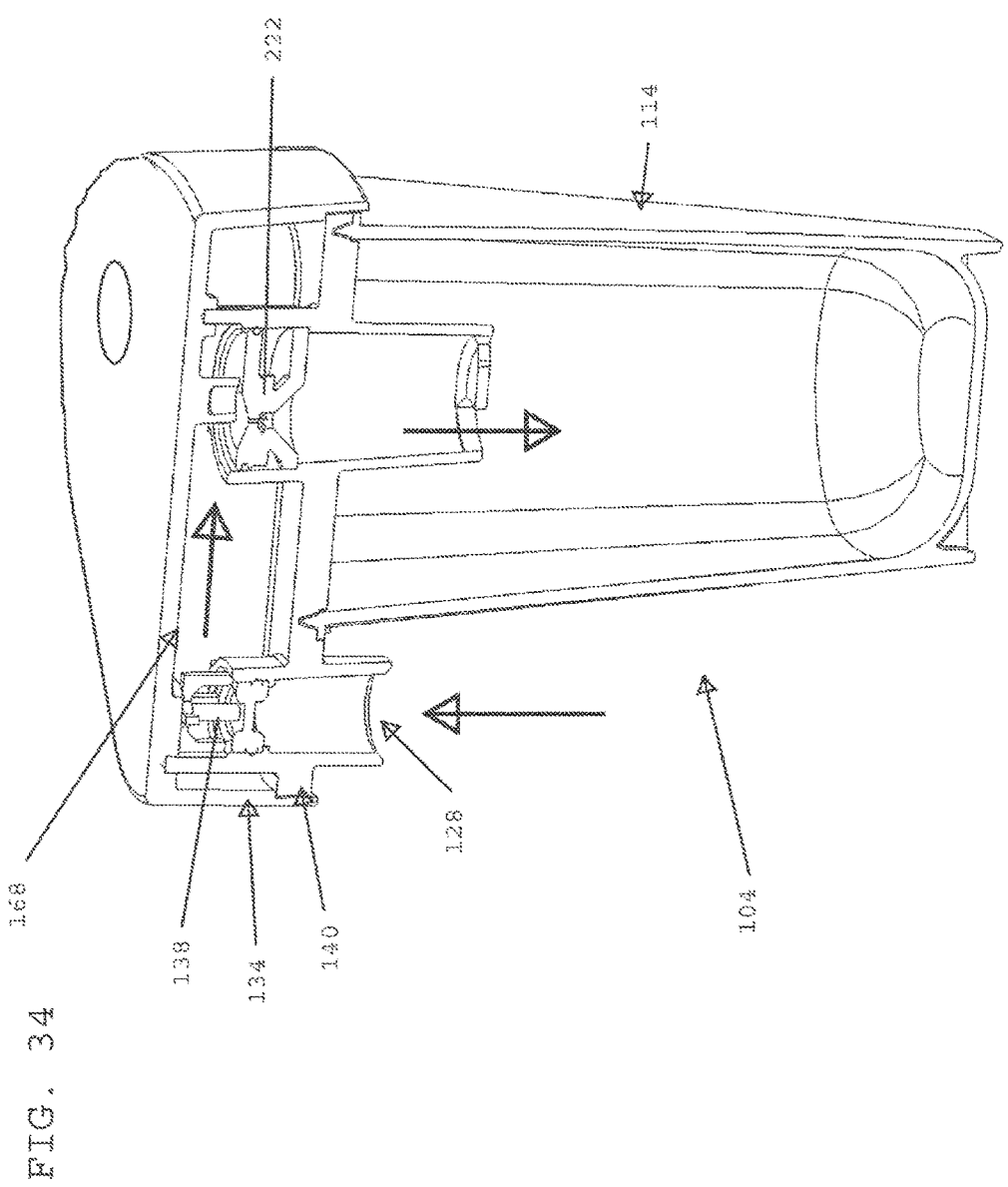
FIG. 34 is a cross-sectional view of the cartridge of FIG. 5, illustrating the flow of gas into the cartridge, through the venturi and into the headspace.
Figure 35:
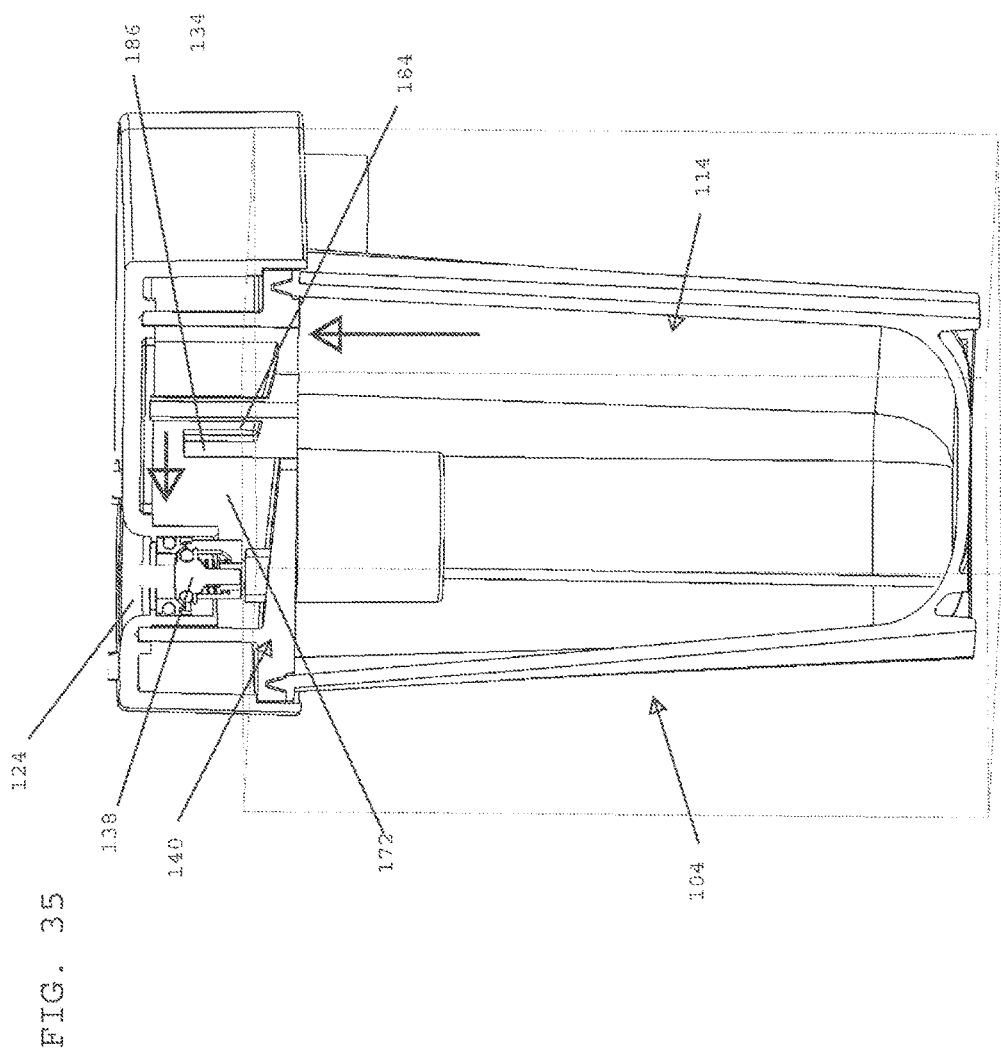
FIG. 35 is a cross-sectional view of the cartridge of FIG. 5, illustrating the flow of gas and diffused liquid from the headspace through the baffle and out of the cartridge.

FIG. 34 illustrates the flow of gas through gas inlet 128, into inlet cavity 168, through venturi 240 of head 222 and into reservoir 114 of cartridge 104. FIG. 35 illustrates the flow of gas and atomized liquid from within reservoir 114 through opening 184 into outlet cavity 172, across bulkhead 186 and out of cartridge 104 through opening 124.

Figure 36:
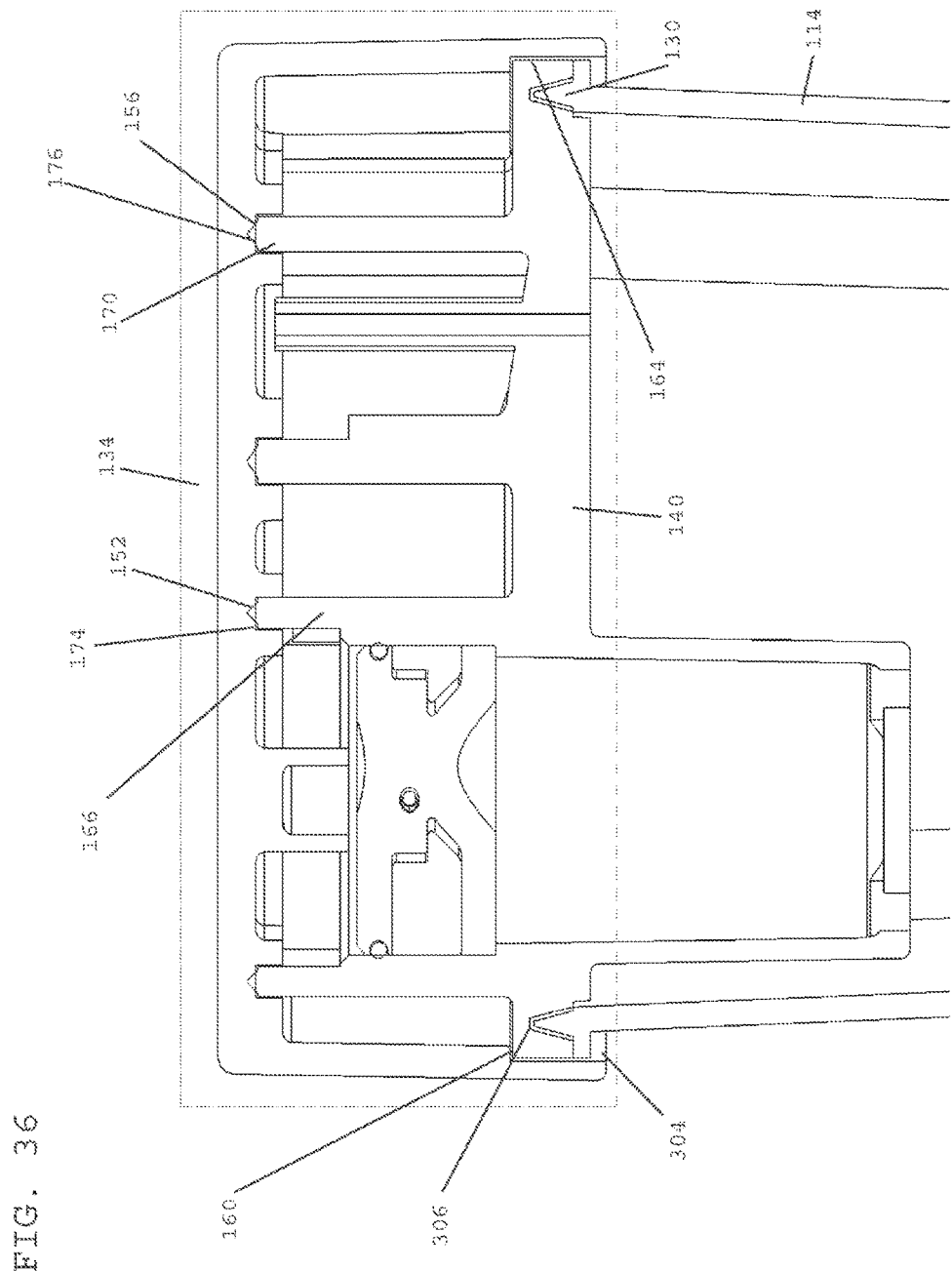
FIG. 36 is a cross-sectional view of the cartridge of FIG. 5, illustrating the connection between the baffle, the cap and the reservoir.

FIG. 36 illustrates a preferred manner of securing cap 134 to baffle 140 and baffle 140 to reservoir 114. At upper edge 176 of wall 170, baffle 140 may be ultrasonically welded to cap 134 within groove 156. Groove 156 and wall 170 cooperate to provide a seal against the mixed gas and atomized liquid from flowing into or out of outlet cavity 172 except through one of the openings provided. Similarly, upper edge 174 of wall 166 of baffle 140 may be ultrasonically welded to cap 134 within groove 152 to provide a seal preventing gas or liquid from exiting from inlet cavity 168 except through one of the openings provided. Outer edge 164 of baffle 140 may cooperate with ledge 160 of cap 134 to provide engagement about the perimeter of the cap and baffle. It may not be necessary to secure these outer edges or surface to each other, as the connection along the tops of wall 166 and 170 should be sufficient to hold the parts together. However, these outer edges and ledges do provide adequate binding surfaces if it is desirable to necessary to have additional securement between the cap and the baffle. Such securement could be physical or chemical bonding or some means of welding the pieces together.

Along upper edge 130 of reservoir 114 may be a lip 304 and formed within baffle 140 may be a mating recess 306. These two features may be configured to engage each other and provide a firm engagement of the reservoir to the baffle and to seal liquid 116 within cartridge 104. Lip 304 and recess 306 may be joined by physically, such as by spin welding or other common techniques. Alternatively, baffle 140 and reservoir 114 may be joined by chemical of physical bonding, such as with an adhesive. It is desirable, regardless of the technique or bonding used, that the connection between baffle 140 and reservoir 114, that a seal be formed preventing liquid 116 from escaping from within cartridge 104, regardless of the orientation of the cartridge.

Figure 37:
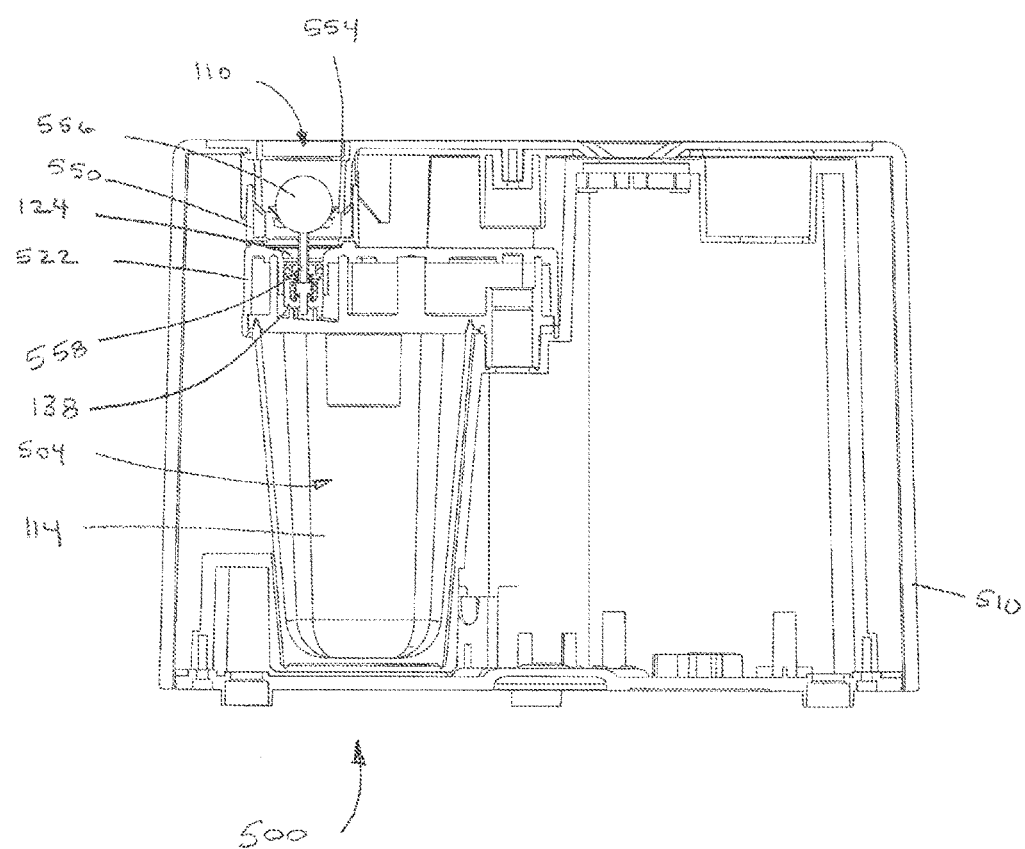
FIG. 37 is a side cross-sectional view of an alternative embodiment of a liquid diffusion device according to the present disclosure with an anti-spill feature.
Figure 37A:
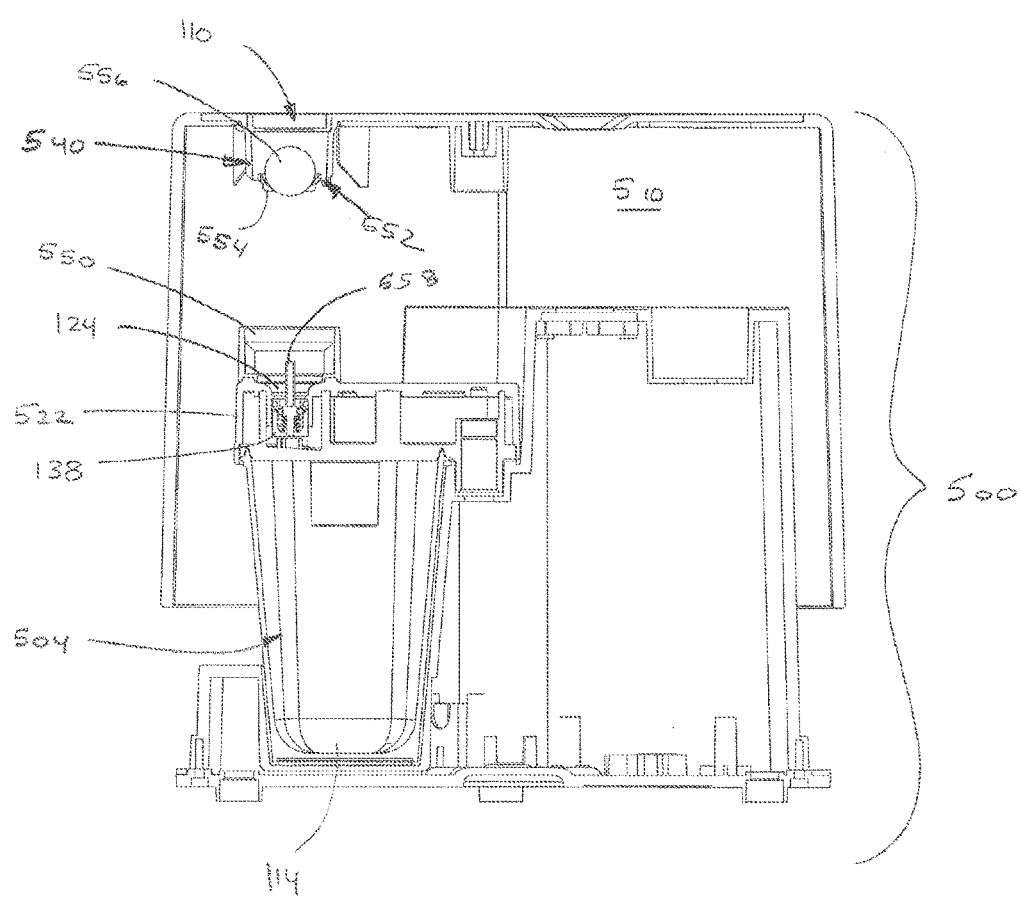
FIG. 37a is a side cross-sectional view of the liquid diffusion device of FIG. 37, with the cover partially exploded from the housing.

FIGS. 37 and 37a illustrate an alternative embodiment liquid diffusion device 500 within which is mounted a removable liquid cartridge 504. Cartridge 504 is generally constructed like cartridge 104, above, with the addition of a fitting 550 extending from a head 522 about opening 124. As shown, fitting 550 is a circumferential wall or bulkhead which aids in the positioning of an anti-spill feature of a cover 510. It is anticipated that a variety of shapes and configurations of fitting 550 will provide the desired positioning aid and it is not intended to limit the nature of the fitting to any particular construction.

Cover 510 includes an interior valve engagement or actuating assembly 540 positioned about outlet 110 and extending toward cartridge 504. Assembly 540 may include a cage 552 with a tapered cartridge engaging portion 554. Positioned within cage 552 may be a ball 556, which is sized to allow free movement within cage 552 but not permit removal of ball 556 through outlet 110. Extending from within cage 552 and toward cartridge 504 may be a valve actuating pin 558. A first end of pin 558 may be configured to engage one way flow device 138 of cartridge 504. A second opposite end of pin 558 extends within cage 552 through tapered end 554 and is engaged by ball 556. Alternatively, pin 558 may be formed integrally with one way flow device 138.

Figure 38:
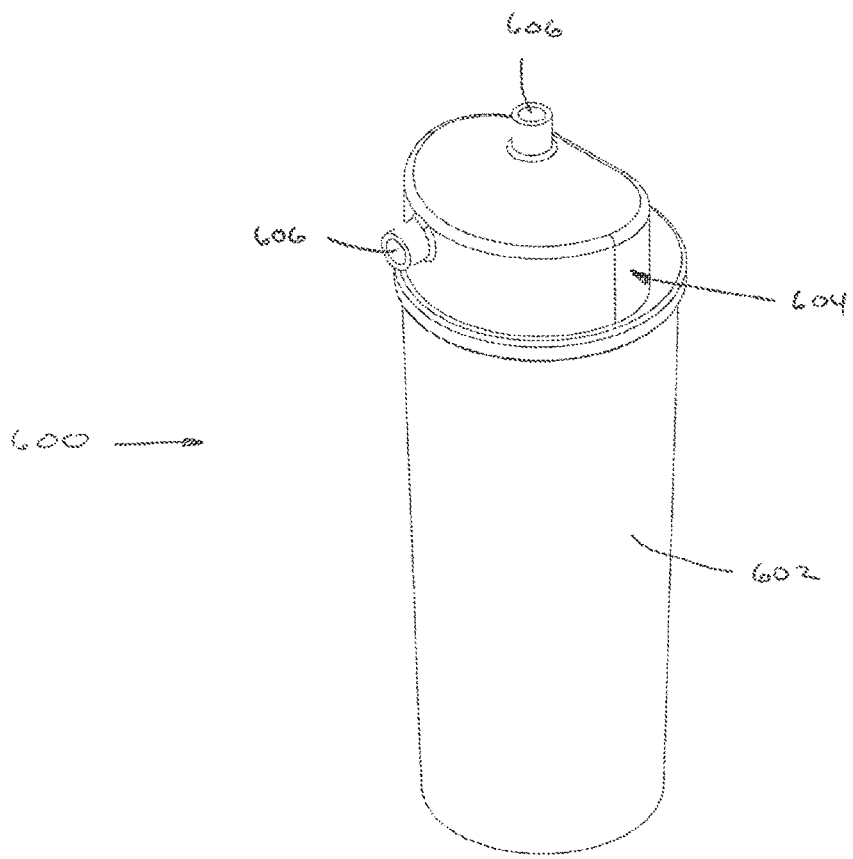
FIG. 38 is a perspective view of a further embodiment of a replaceable liquid cartridge according to the present disclosure.
Figure 39:
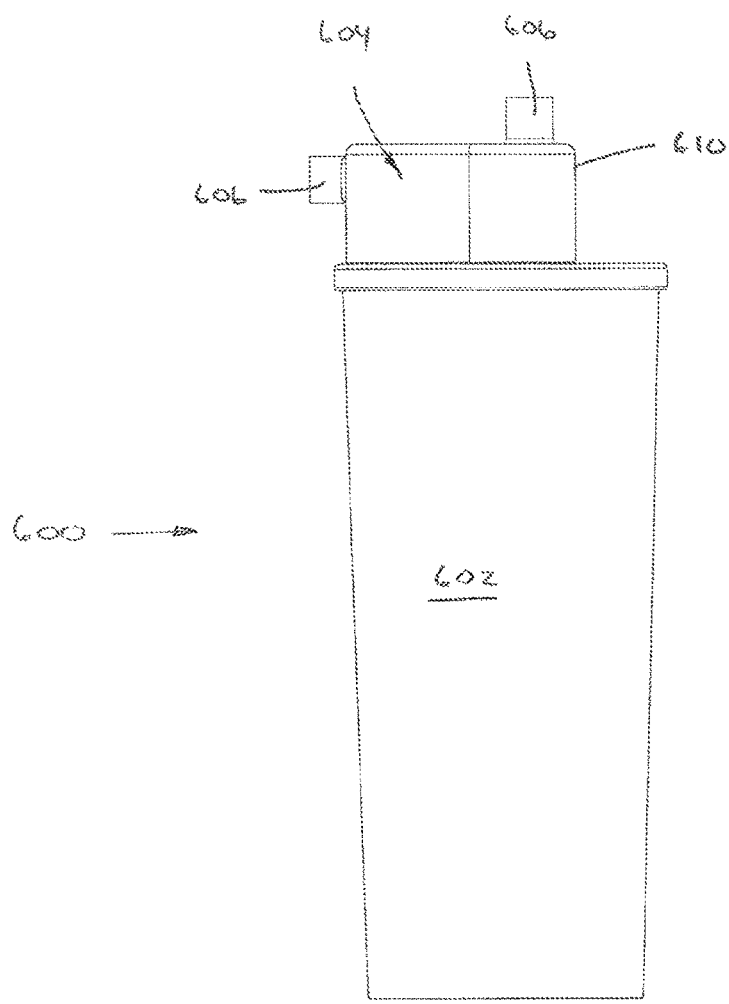
FIG. 39 is a side view of the cartridge of FIG. 38.
Figure 40:
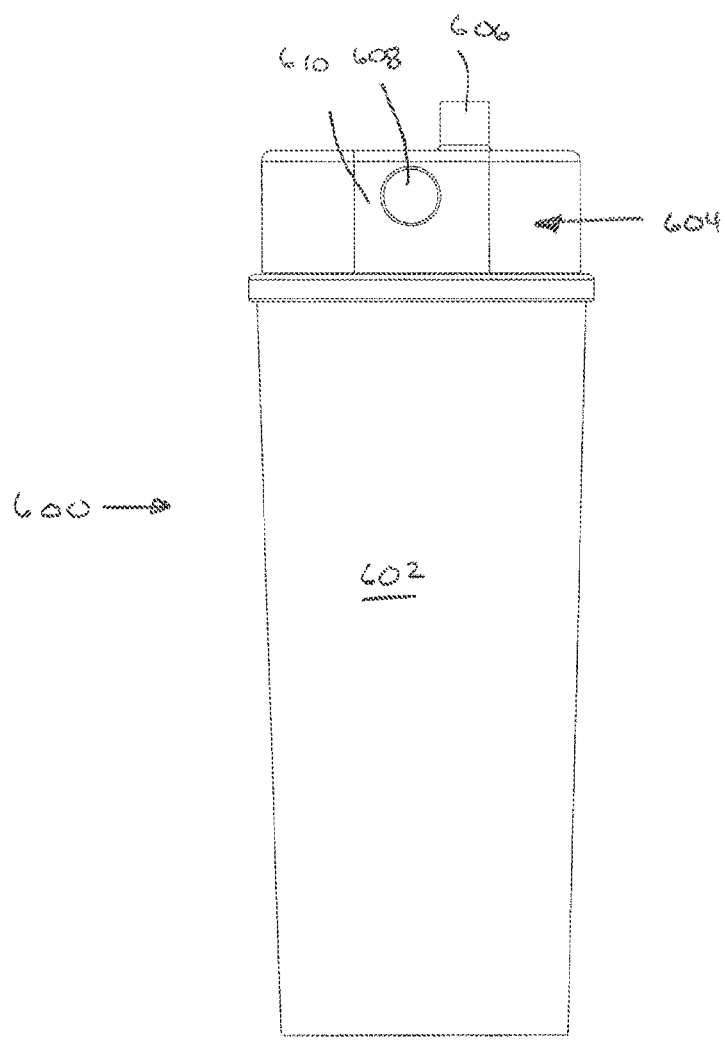
FIG. 40 is a rear view of the cartridge of FIG. 38.
Figure 41:
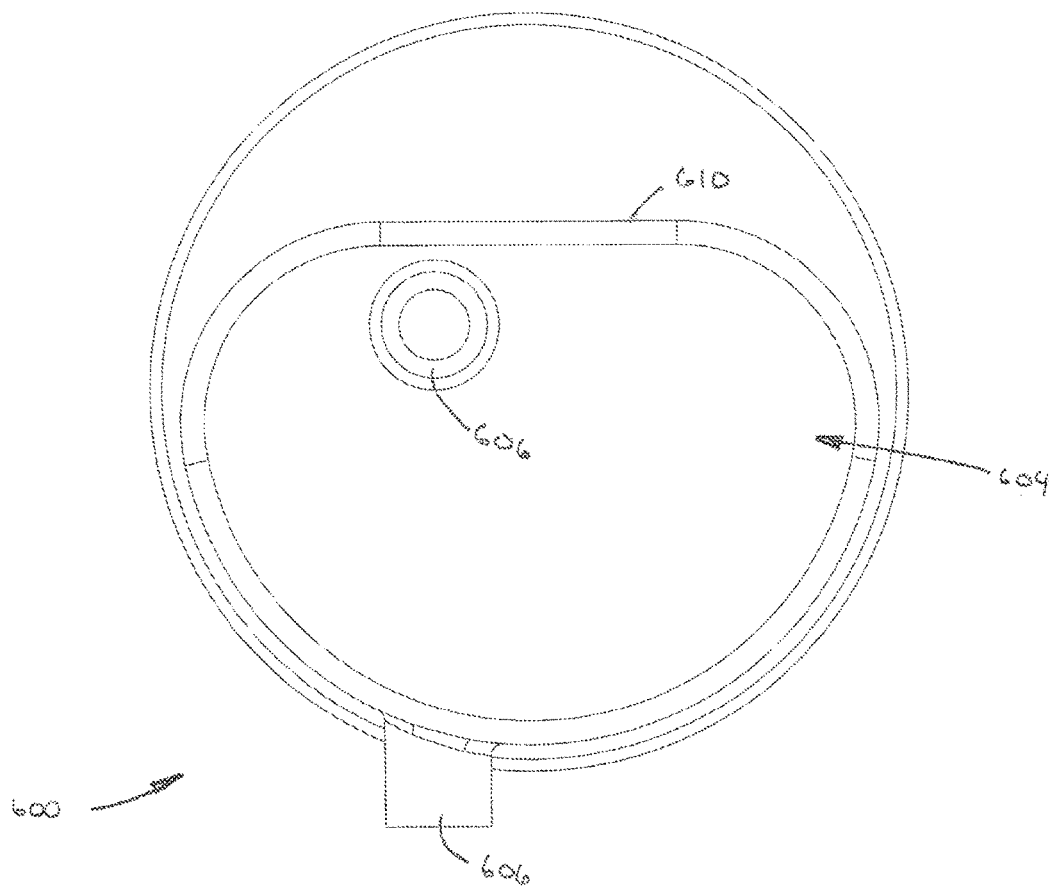
FIG. 41 is a top view of the cartridge of FIG. 38.

When cover 510 is placed onto device 500 with cartridge 504 in recess 112, fitting 550 engages tapered end 554 of cage 552 and positions pin 558 to engage one way flow device 138. Pin 558 should move freely enough and be sufficiently light so that merely placing the cover about the cartridge does not depress one way flow device 138 and open the flow device to permit passage of gas and liquid. When device 500 is in a generally upright position, as shown in FIG. 38, ball 556 engages the inner end of pin 558 and provides enough weight to depress and open one way flow device 138. So engaged, device 500 may be operated to diffuse liquid within cartridge 504 and have the liquid and gas mix escape from the cartridge and device 500.

However, if device 500 is tipped beyond a certain amount from upright, ball 556 would no longer be providing sufficient force to pin 558 to depress and open one way flow device 138. Thus, the liquid and gas mix or liquid by itself may not exit from cartridge 504 once device 500 is tipped too far from upright. Since device 500 may be configured to rest of a table or other flat horizontal surface, it may be desirable to have a device to prevent accidental spills of liquid of the device is knocked over or overly tipped while being moved. Other configurations of anti-spilling or tip sensing devices may be incorporated into device 500 and it is not intended to limit the nature of these spill prevention features to the particular features illustrated herein.

Figure 42:
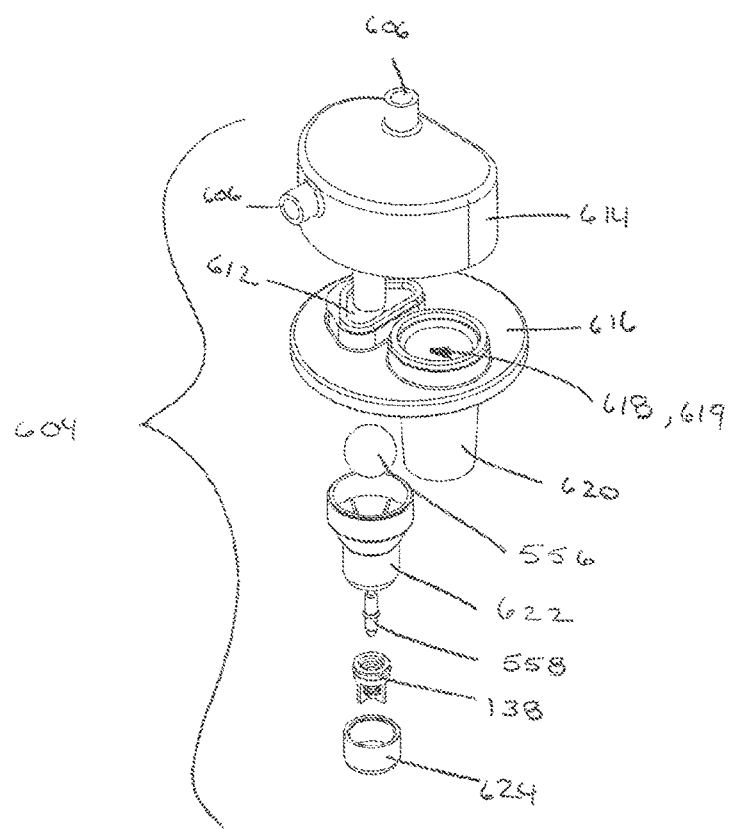
FIG. 42 is an exploded perspective view of a cartridge head assembly for the cartridge of FIG. 38.

Referring now to FIGS. 38 to 42, an alternative embodiment cartridge 600 is shown which includes a reservoir 602 and a cartridge head assembly 604. A pair of outlets 606 are provided so that cartridge 600 may be used in installations where it is desired to have a plume of diffused liquid and air dispersed either horizontally or vertically. As shown in FIG. 42, both outlets 606 are in fluid communication with an outlet cavity 612 within head assembly 604. Either one or both of the outlets may be left open to permit the gas/liquid diffusion to escape from cartridge 600. One of the outlets 606 may be blocked or sealed to force all exiting liquid and gas to exit through the other outlet 606. Head assembly 604 also includes a gas inlet 608 in a rear face 610. Inlet 608 is configured to receive a bayonet or similar type of interface to a source of pressurized gas for diffusing a liquid with the reservoir and ejected the gas and liquid diffusion from the reservoir into a space to be treated.

As mentioned above, head assembly 604 and reservoir 602 may be jointed to each other by heat or ultrasonic welding, spin welding, or by use of an adhesive.

Referring now to FIG. 42, head assembly 604 includes a upper cap 614 and a baffle 616. An opening 618 is defined to receive a head 222 and extends into an initial expansion chamber 619. This is configured similar to openings 180 and 200 of baffle 140, above. These openings 618 and 619 are in fluid communication with inlet 612 and air flowing through inlet 612 will draw liquid from reservoir 602 into head 222 and diffuse it back into a headspace within reservoir 602, as described above.

An anti-spill feature may also be included in head assembly 604. This is provided by ball 556 nested between baffle 616 and a ball cage 622. A pin extends from cage 622 to engage one-way flow device 138, which may be held in place by a lower cover 624. Operation of this ball-activated spill preventer is similar to that described with regard to FIG. 37, above. When cartridge 600 is tilted from vertical sufficiently to displace ball 556 from atop pin 558, one-way flow device 138 forces itself into a closed position and prevents liquid from flowing from reservoir 604 and out of cartridge through one or both outlets 606. Cartridge 600 includes this ant-spill feature integrally, as opposed to the incorporation of the anti-spill feature into cover 510, as shown in FIG. 37. It is anticipated that a cartridge suitable for use with diffusion device 100 may be adapted to include the anti-spill feature of cartridge 600.

Cartridge 600 is configured to be used either mounted within a known diffusion device or may be used on a non-enclosed installation including a mating bayonet fitting providing pressurized gas. Such a fitting could be located within ductwork or a plenum for supplying diffused liquid through a facility served by the ductwork or plenum. In this fashion, the controller could be mounted remotely from the cartridge, and such a controller may be used to control more than one diffusion device. Such a non-enclosed mounting arrangement may also be suitable for more industrial or utilitarian installations, where enclosure of the cartridge and control mechanism are not as aesthetically desirable or required.

Figure 43:
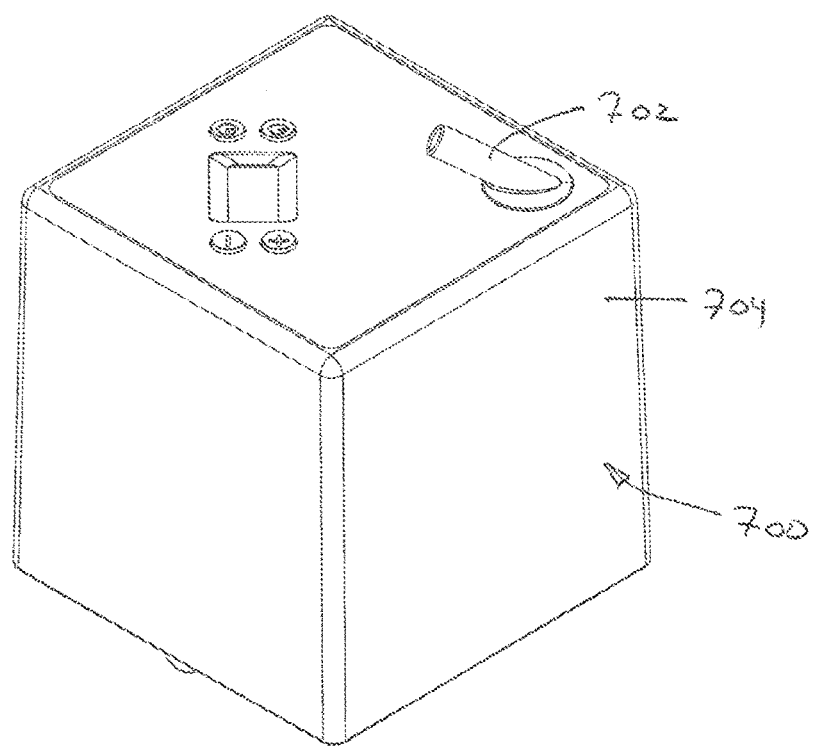
FIG. 43 is a perspective view of an alternative embodiment of a diffusion device according to the present disclosure.
Figure 44:
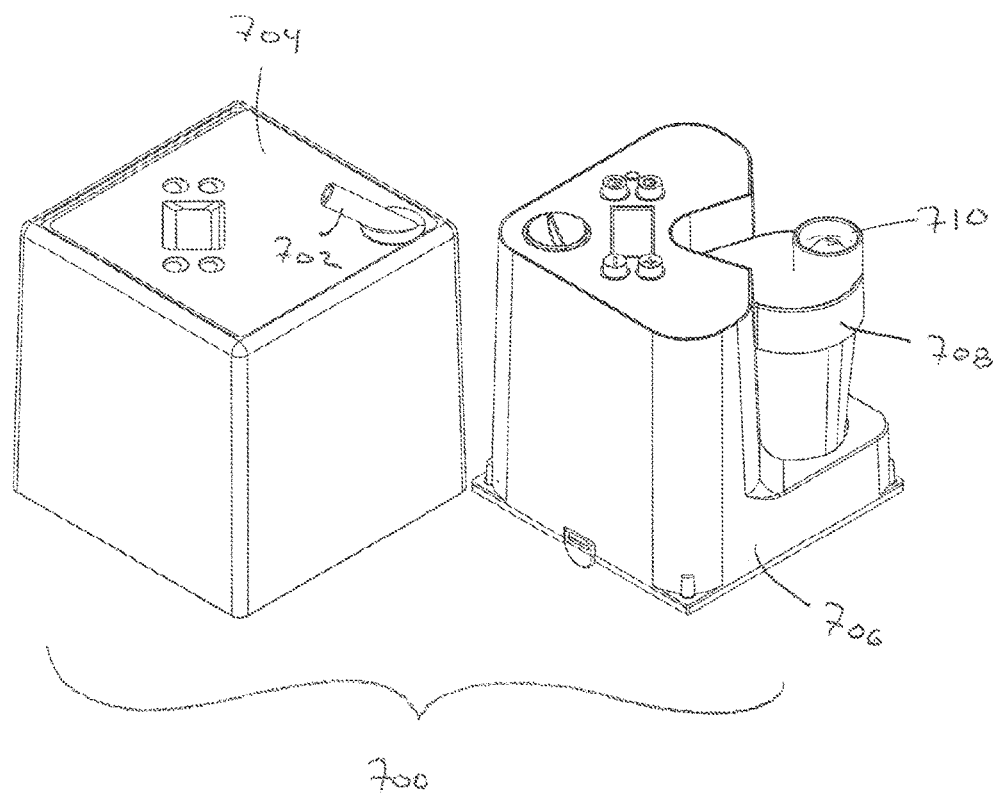
FIG. 44 is a perspective view of the diffusion device of FIG. 43, with the cover removed and resting adjacent the base.

FIGS. 43 and 44 illustrate an alternative diffusion device 700 with a directional outlet 702 included with a removable cover 704. Directional outlet 702 allows device 700 to be placed in a location where there may be a closely adjacent overhanging object, for example, on a shelf with the next higher shelf near a top of device 700. Directional outlet 702 permits the initial direction of the dispersion of the liquid/gas mixture to be directed out of the shelf and into the space to be treated. Preferably, directional outlet 702 is pivotably attached to cover 704 and may be directed to point in any direction. Directional outlet 702 may also be directed into a ducting system, such as for a HVAC system connected to the space to be treated. Directional spout 702 may also provide an attachment point for a conduit to direct a flow of gas and diffused liquid into such a ducting system if it is not convenient or feasible to mount device 700 in immediate proximity to or within the ductwork.

Referring now to FIG. 44, device 700 includes a base 706 with a recess for removably receiving a cartridge 708, and about which cover 704 may be positioned. Cartridge 708 includes an anti-spill feature 710 about an exit point for releasing the liquid/gas mixture from the cartridge and into directional outlet 702. Anti-spill feature may be configured similarly to the ball-and-pin engagement of a one-way flow device, as described above with regard to cartridge 600.

Figure 45:
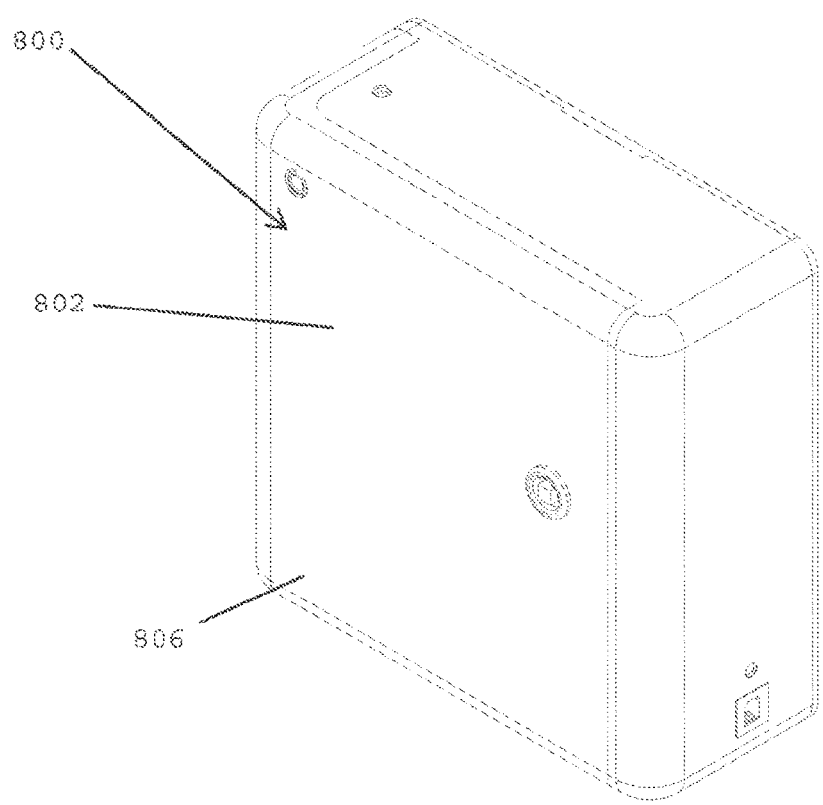
FIG. 45 is a perspective view of a wall mount embodiment of a liquid diffusion device according to the present disclosure.
Figure 46:
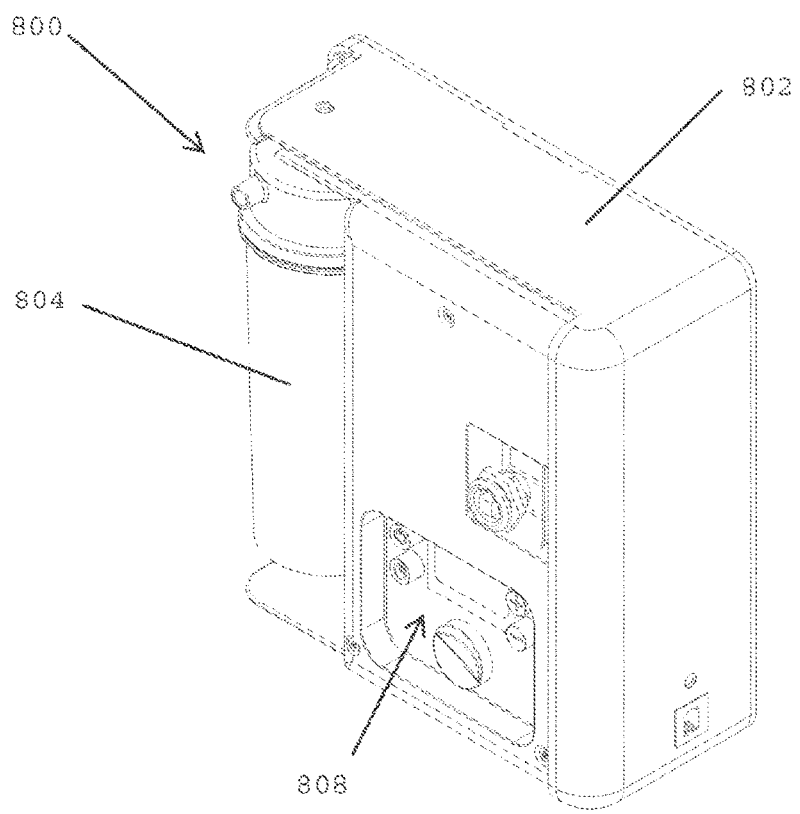
FIG. 46 is a perspective view of the device of FIG. 45 with a door removed.

Referring now to FIGS. 45 and 46, a diffusion device 800 includes a housing 802 configured to provide flexible mounting or placement. A replaceable cartridge 804 is shown within the housing and device 800 and cartridge 804 are configured similarly to other devices and cartridges described herein. Housing 802 is configured to permit placement on a surface similar to device 100, above. Housing 802 is also configured to permit easy wall or bulkhead mounting, including a door 806 instead of a removable cover to access cartridge 804 and controls 808 positioned within housing 802. Device 800 may be mounted to a wall of a room or space to be treated in a discrete or relatively non-visible location for aesthetic purposes. Device 800 may also be mounted within ductwork such as might be part of an HVAC system of the space to be treated. When mounted within such a ductwork or HVAC system, device 800 may be used to treat multiple discrete spaces that might have required more than one device 100.

Figure 47:
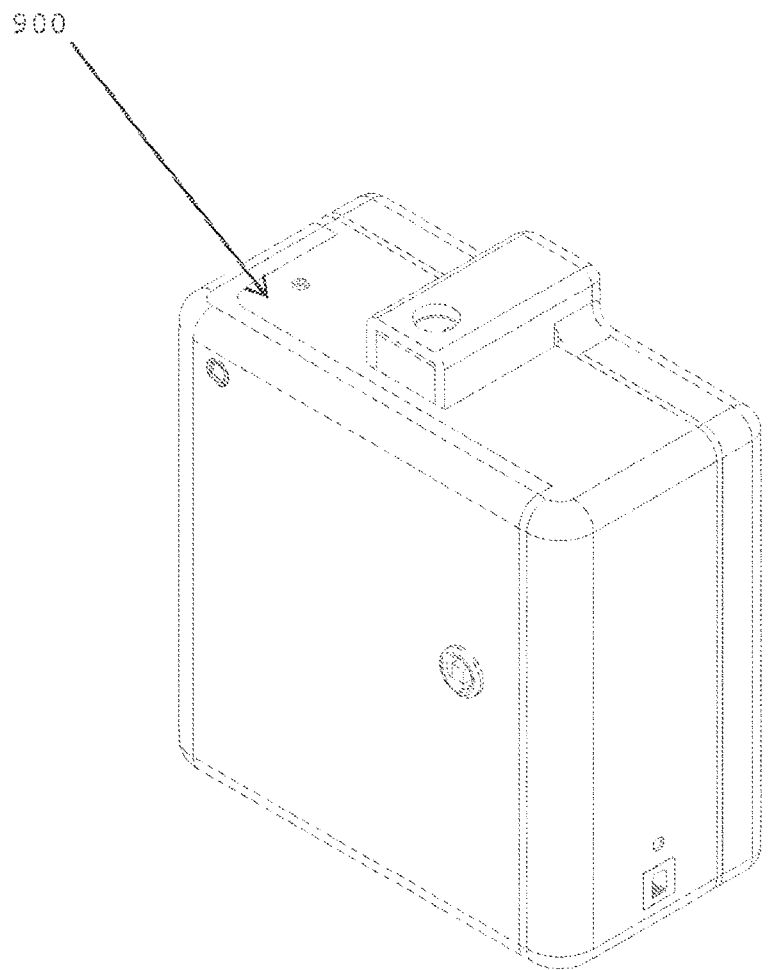
FIG. 47 is a perspective view of an overhead mount embodiment of a liquid diffusion device according to the present disclosure.
Figure 48:
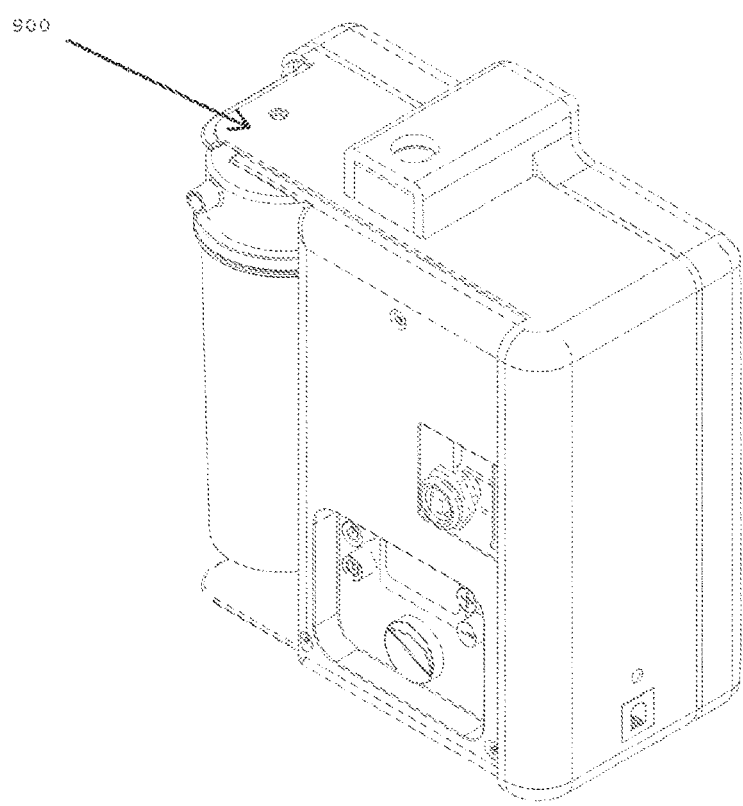
FIG. 48 is a perspective view of the device of FIG. 47 with a door removed.

FIGS. 47 and 48 illustrate a further embodiment of a diffusion device according 900 to the present invention.

Device 900 is similarly configured to device 800 but is adapted for mounting to an overhead fixture, such as a light fixture or a track lighting fixture.

It may also be noted that the various diffusion devices disclosed above have included some form of operational control, such as controls for varying the speed or timing of operation of an on-board air compressor to provide gas flow through the cartridge. In addition to using such controls to alter the amount of liquid diffused by the devices and the amount of treatment of a space, the characteristics of the liquid to be diffused and the amount of liquid within the reservoir may also alter the amounts. More viscous liquids may diffuse more slowly. Lower liquid levels within the reservoir will create a greater head to be overcome within the siphon tube to draw liquid into the venturi for diffusion. The density of the liquid may also affect the amount of treatment provided. These characteristics of the cartridge may also be taken into account when setting controls regarding the function and operation of the diffusion devices into which the cartridges are received.

It is also anticipated that a cartridge according to the present disclosure may include several reservoirs with different liquids or compounds. Each of these reservoirs may be in fluid communication with a common expansion chamber of the cartridge. A single common venturi may be provided through the pressurized gas may flow to diffuse the different compounds or liquids at the same time. Alternatively, such a multi-reservoir cartridge may have a single expansion chamber and a plurality of venturis. Each of the different reservoirs could be in fluid communication with one of the venturis and pressurized gas flow would individually diffuse the compounds or liquids into the common expansion chamber for dispersion within the space to be treated. It may desirable to have different treatment compounds separated until diffusion due to reactions or interactions between different compounds or due to decay characteristics of the different compounds. The liquids to be diffused may be immiscible and thus not suited for containment within the same reservoir. The different cartridge embodiments and diffusion device embodiments of the present disclosure may be adapted to include such a multiple compound concept.

While the invention has been described with reference to preferred embodiments, it is to be understood that the invention is not intended to be limited to the specific embodiments set forth above. Thus, it is recognized that those skilled in the art will appreciate that certain substitutions, alterations, modifications, and omissions may be made without departing from the spirit or intent of the invention. Accordingly, the foregoing description is meant to be exemplary only, the invention is to be taken as including all reasonable equivalents to the subject matter of the invention, and should not limit the scope of the invention set forth in the following claims.

What is claimed is:

1. A cartridge for use with a liquid diffusing device, the diffusing device including a flow of gas, the cartridge comprising:
   a reservoir and a diffusion head permanently attached to the reservoir;
   the reservoir defining an interior space partially filled with a liquid to be diffused and a head space above the liquid within the reservoir;
   the diffusion head comprising:
   a venturi opening into the head space;
   a conduit including a first end extending below the liquid level in the reservoir, a second end of the conduit adjacent to and in fluid communication with the venturi;
   a cartridge inlet in fluid communication with the venturi and permitting the flow of gas into the venturi, the venturi configured to permit gas to flow from the cartridge inlet through the venturi and into the head space of the reservoir;
   an outlet in fluid communication with the head space permitting gas within the head space to enter an outlet cavity;
   wherein the outlet comprises an outlet cavity extending between an outlet cavity inlet into the head space and an outlet cavity outlet; and,
   the cartridge inlet and the outlet cavity configured to selectively prevent liquid from within the reservoir from exiting the cartridge;
   the outlet further including a one way flow device mounted in the outlet cavity that prevents liquid that has not been diffused from passing through the outlet cavity and out of the cartridge; and
   the outlet cavity further including a transverse bulkhead positioned between the outlet cavity inlet and outlet cavity outlet, the bulkhead defining a first outlet section adjacent the outlet cavity inlet and a second outlet section adjacent the outlet cavity outlet, the transverse bulkhead preventing liquid within the second outlet section from flowing into the first outlet section, the second outlet section further including a weep hole to permit liquid within the second cavity to drain into the reservoir.

2. The cartridge of claim 1, wherein the second outlet section has a small volume in relation to a volume of the reservoir.

* * * * *